United States Patent
Evdokimov et al.

(10) Patent No.: US 11,993,647 B2
(45) Date of Patent: May 28, 2024

(54) ANTIBODY OR AN ANTIGEN-BINDING FRAGMENT THEREOF CAPABLE OF BINDING TO A HUMAN RECEPTOR OF INTERLEUKIN-6

(71) Applicant: JOINT STOCK COMPANY "BIOCAD", St. Petersburg (RU)

(72) Inventors: Stanislav Rudolfovich Evdokimov, Puschino (RU); Andrei Borisovich Ulitin, Puschino (RU); Valery Vladimirovich Solovyev, Pushchino (RU); Aleksei Aleksandrovich Aleksandrov, Perm (RU); Yulia Sergeevna Chernykh, Solikamsk (RU); Timofey Aleksandrovich Nemankin, St. Petersburg (RU); Anna Konstantinovna Vladimirova, St. Petersburg (RU); Oleg Igorevich Smotrov, Ramon' (RU); Tatiana Veniaminovna Chernovskaya, Lyubuchany (RU); Aleksandr Aleksandrovich Moshchenko, Klincy (RU); Viktoriia Evgenevna Nalobina, Tutaev (RU); Roman Alekseevich Ivanov, Moscow (RU); Dmitry Valentinovich Morozov, Moscow (RU)

(*) Notice: Subject to any disclaimer, the term of this patent is extended or adjusted under 35 U.S.C. 154(b) by 1280 days.

(21) Appl. No.: 16/325,528

(22) PCT Filed: Aug. 3, 2017

(86) PCT No.: PCT/RU2017/050070
§ 371 (c)(1),
(2) Date: Feb. 14, 2019

(87) PCT Pub. No.: WO2018/034597
PCT Pub. Date: Feb. 22, 2018

(65) Prior Publication Data
US 2019/0194313 A1 Jun. 27, 2019

(30) Foreign Application Priority Data
Aug. 17, 2016 (RU) .............................. 2016133720

(51) Int. Cl.
| | | |
|---|---|---|
| C07K 16/24 | (2006.01) |
| A61K 9/00 | (2006.01) |
| A61K 9/19 | (2006.01) |
| A61K 39/395 | (2006.01) |
| A61P 37/00 | (2006.01) |
| A61P 37/06 | (2006.01) |
| A61P 37/08 | (2006.01) |
| C07K 16/06 | (2006.01) |
| C07K 16/18 | (2006.01) |
| C12N 15/00 | (2006.01) |
| C12N 15/63 | (2006.01) |

(52) U.S. Cl.
CPC .......... *C07K 16/248* (2013.01); *A61K 9/0073* (2013.01); *A61K 9/19* (2013.01); *A61K 39/395* (2013.01); *A61P 37/00* (2018.01); *A61P 37/06* (2018.01); *A61P 37/08* (2018.01); *C07K 16/065* (2013.01); *C07K 16/18* (2013.01); *C07K 16/24* (2013.01); *C12N 15/00* (2013.01); *C12N 15/63* (2013.01)

(58) Field of Classification Search
CPC ..................................................... C07K 16/28
See application file for complete search history.

(56) References Cited

U.S. PATENT DOCUMENTS

| | | |
|---|---|---|
| 8,673,306 B2 | 3/2014 | Shulok et al. |
| 2007/0280945 A1 | 12/2007 | Stevens et al. |
| 2011/0177074 A1 | 7/2011 | Sivakumar et al. |
| 2011/0245473 A1 | 10/2011 | Igawa et al. |
| 2015/0125450 A1 | 5/2015 | Goldenberg et al. |

FOREIGN PATENT DOCUMENTS

| | | |
|---|---|---|
| CN | 1162922 A | 10/1997 |
| CN | 102585002 A | 7/2012 |
| CN | 105037548 A | 11/2015 |
| CN | 105617387 A | 6/2016 |
| EP | 2206775 B1 | 7/2010 |
| JP | 2009-539349 A | 11/2009 |
| JP | 7158376 B2 | 10/2022 |
| RU | 2550262 C1 | 5/2015 |
| RU | 2550262 C1 | 5/2015 |
| WO | 2007/143168 A2 | 12/2007 |
| WO | 2010/148223 A2 | 12/2010 |
| WO | 2012/118813 A2 | 9/2012 |
| WO | WO 2015/065987 A1 | 5/2015 |

OTHER PUBLICATIONS

Corresponding European patent application No. 17841757.2 examination report dated Dec. 12, 2022.
Mathieu Dondelinger et al., Understanding the Significance and Implications of Antibody Numbering and Antigen-Binding Surface/Residue Definition. Front. Immunol., Oct. 16, 2018. Sec. Vaccines and Molecular Therapeutics. vol. 9—2018 | https://doi.org/10.3389/fimmu.2018.02278.
Wei Li et al., Antibody Aggregation: Insights from Sequence and Structure. Antibodies 2016, 5(3), 19; https://doi.org/10.3390/antib5030019.

(Continued)

*Primary Examiner* — Prema M Mertz

(57) ABSTRACT

The invention relates to medicine. The problem addressed by the present invention consists in creating alternative antibodies or fragments thereof which are capable of specifically binding to a human receptor of interleukin-6 and which would be useful as drugs for treating or diagnosing diseases, or for relieving symptoms, mediated by interleukin-6.

11 Claims, 10 Drawing Sheets

Specification includes a Sequence Listing.

(56) References Cited

OTHER PUBLICATIONS

Peter C. Heinrich et al., Principles of interleukin (IL)-6-type cytokine signalling and its regulation. Biochem J (2003) 374 (1): 1-20.
Simon A. Jones et al., The soluble interleukin 6 receptor: mechanisms of production and implications in disease. vol. 15, Issue1, Jan. 2001, pp. 43-58.
Pluckthun. Antibodies from Escherichia coli. Oct. 4, 1990, Nature, vol. 347, No. 6292, pp. 497-498.
William R.Pearson, [5] Rapid and sensitive sequence comparison with FASTP and FASTA. Methods in Enzymology, vol. 183, 1990, pp. 63-98.
William R Pearson. Flexible Sequence Similarity Searching with the FASTA3 Program Package. Jan. 2000. Methods in Molecular Biology, 132:185-219.
William R Pearson. Empirical statistical estimates for sequence similarity searches. Journal of Molecular Biology (JMB). vol. 276, Issue 1, Feb. 13, 1998, pp. 71-84.
Hans J. de Haard et al., A Large Non-immunized Human Fab Fragment Phage Library That Permits Rapid Isolation and Kinetic Analysis of High Affinity Antibodies. JBC (Journal of Biological Chemistry). Protein Chemistry and Structure| vol. 274, Issue 26, p. 18218-18230, Jun. 1999.
Tristan J. Vaughan et al., Human Antibodies with Sub-nanomolar Affinities Isolated from a Large Non-immunized Phage Display Library. Nature Biotechnology vol. 14, pp. 309-314 (1996).
The corresponding European patent application No. 17841757.2 extended search report dated Mar. 19, 2020.
Tom W J Huizinga et al., "Sarilumab, a fully human monoclonal antibody against IL-6Rα in patients with rheumatoid arthritis and an inadequate response to methotrexate: efficacy and safety results from the randomised SARIL-RA-Mobility Part A trial", Annals of the Rheumatic Diseases, vol. 73, No. 9, Dec. 2013 (Dec. 2, 2013), pp. 1626-1634.
Mihara M et al., "Tocilizumab inhibits signal transduction mediated by both mIL-6R and sIL-6R, but not by the receptors of other members of IL-6 cytokine family", International Immunopharmacology. vol. 5, Issue 12, Nov. 2005, pp. 1731-1740.
Smolen et al: "Effect of interleukin-6 receptor inhibition with tocilizumab in patients with rheumatoid arthritis (OPTION study): a double-blind, placebo-controlled, randomised trial ", He Lancet, Elsevier, Amsterdam, NL, vol. 371, No. 9617, Mar. 22, 2008 (Mar. 22, 2008), pp. 987-997.
John D Isaacs et al., "Therapy with Monoclonal Antibodies. II. The Contribution of Fcγ Receptor Binding and the Influence of CH1 and CH3 Domains on In Vivo Effector Function ",The Journal of Immunology, vol. 161, No. 8, Oct. 15, 1998 (Oct. 15, 1998), pp. 3862-3869.
Armour K L et al., "Recombinant human IgG molecules lacking Fcγ receptor I binding and monocyte triggering activities ",European Journal of Immunology, Wiley VCH, Weinheim, vol. 29, No. 8, Aug. 1, 1999 (Aug. 1, 1999), pp. 2613-2624.
Ranajoy Majumdar et al., "Correlations between changes in conformational dynamics and physical stability in a mutant IgG1 mAb engineered for extended serum half-life ", MABS, vol. 7, No. 1, Jan. 2, 2015 (Jan. 2, 2015), pp. 84-95.
Anonymous: "Engineered Fc Regions", Review InvivoGen, Jan. 1, 2001 (Jan. 1, 2001), pp. 1-2.
Perez De La Lastra et al., "Epitope mapping of 10 monoclonal antibodies against the pig analogue of human membrane cofactor protein (MCP)", Immunology, vol. 96, No. 4, Apr. 1, 1999 (Apr. 1, 1999), pp. 663-670.
Gershoni Jonathan M et al., "Epitope Mapping-The First Step in Developing Epitope-Based Vaccines", Biodrugs, Adis International Ltd, NZ, vol. 21, No. 3, Jan. 1, 2007 (Jan. 1, 2007), pp. 145-156.
Trispecific F(ab')3 derivatives that use cooperative signaling via the TCR/CD3 complex and CD2 to activate and redirect resting cytotoxic T cells. J Immunol Jul. 1, 1991, 147 (1) 60-69; Abstract.
Pluckthun. Antibodies from *Escherichia coli*. The Pharmacology of Monoclonal Antibodies, vol. 113, Rosenburg and Moore eds., Springer-Verlag, New York, p. 269-315, 1994. Abstract.
William R Pearson. [15] Effective protein sequence comparison. Methods in Enzymology vol. 266, 1996, pp. 227-258. Abstract.
James D.Marks et al., By-passing immunization: Human antibodies from V-gene libraries displayed on phage. vol. 222, Issue 3, Dec. 5, 1991, pp. 581-597; Abstract.
The corresponding Japanese patent application No. 2019-509472 extended search report dated Feb. 1, 2022.
The corresponding Japanese patent application No. 2019-509472 extended search report dated May 7, 2021.
"Fc Engineering", [online], Aug. 15, 2016 cited by Japanese examiner Apr. 27, 2021. Retrieved Feb. 18, 2022. https://web.archive.org/web/20160815235841/https://absoluteantibody.com/antibody-resources/antibody-engineering/fc-engineering/.
PCT/RU2017/050070 International Search Report.
PCT/RU2017/050070 written opinion.
Peter C. Heinrich et al., Principles of interleukin (IL)-6-type cytokine signalling and its regulation, Biochem. J. (2003) 374, 1-20.
Simon A. Jones et al., The soluble interleukin 6 receptor: mechanisms of production and implications in disease, FASEB, vol. 15 Jan. 2011, 43-58.
Corresponding Korean patent application No. 10-2019-7007632 Office Action dated May 26, 2023 (Translation provided).
Corresponding Korean patent application No. 10-2019-7007632 Office Action dated Oct. 27, 2023 (Translation provided).
Maxime Boulet-Audet, et al., High-Throughput Thermal Stability Analysis of a Monoclonal Antibody by Attenuated Total Reflection FT-IR Spectroscopic Imaging. Anal. Chem. 2014, 86, 19, 9786-9793. Publication Date:Sep. 15, 2014. https://doi.org/10.1021/ac502529q.
V Mazurov, et al., FRI0108 Short-Term Efficacy of BCD-089, Novel Monoclonal Anti-IL-6 Receptor Antibody, in Combination With Methotrexate in Patients With Rheumatoid Arthritis: 12-Week Results of Phase 2 Aurora Study. Scientific Abstracts, pp. 637-638, Jun. 5, 2020. Poster Presentations. Friday, Jun. 14, 2019Rheumatoid arthritis—biological DMARDs. https://ard.bmj.com/content/78/Suppl_2/721.1.
V Mazurov, et al., FRI0114 Efficacy of Levilimab, Novel Monoclonal Anti-IL-6 Receptor Antibody, in Combination With Methotrexate in Patients With Rheumatoid Arthritis: 1-Year Results of Phase 2 Aurora Study. Scientific Abstracts. Poster PresentationsFriday, Jun. 5, 2020Rheumatoid arthritis—biological DMARDs. https://ard.bmj.com/content/79/Suppl_1/637.2.
The corresponding Chinese patent application No. 20178064176 office action and search report dated Jun. 28, 2022.

ANTIBODY OR AN ANTIGEN-BINDING FRAGMENT THEREOF CAPABLE OF BINDING TO A HUMAN RECEPTOR OF INTERLEUKIN-6

FIELD OF THE INVENTION

The present invention relates to medicine. The present invention relates to development of antibodies or fragments thereof capable of specific binding to the human interleukin-6 receptor, which could be used as drugs for treating or diagnosing diseases or alleviating interleukin-6-mediated symptoms. The invention also relates to methods of producing said antibodies and a method of treating human diseases with using said antibodies.

BACKGROUND OF THE INVENTION

Interleukin-6 (IL-6) is one of the main mediators of inflammatory responses produced by a wide range of antigen-presenting cells, including B and T cells. IL-6 is produced by activated monocytes or macrophages, endothelial cells, fibroblasts, activated T cells, as well as a range of cells which are not immunocytes. Along with many other cytokines it is involved in processes related to immune response, angiogenesis, inflammation, bone metabolism. The main effect of IL-6 is associated with its participation as a co-factor in the differentiation of B lymphocytes, their maturation and transformation into plasma cells secreting immunoglobulins. Besides that, IL-6 promotes IL-6 receptor expression on activated immunocytes, as well as induces production of IL-2 by T cells. This cytokine stimulates proliferation of T lymphocytes and hematopoiesis responses. In terms of variety of cell sources of products and targets for biological effects, interleukin-6 is one of the most active cytokines involved in realization of immune and inflammatory response. It was shown that the disbalance between pro- and antiinflammatory effects of IL-6 results in various autoimmune diseases; chronic inflammation and osteoporosis, psoriasis, while its excessive production results in different forms of cancer.

In this connection, blocking of IL-6 effect is an attractive aim for investigations and treatment of said diseases (PeterC.HeinrichBiochem. J. (2003) 374:1).

Transduction of cytokine signal inside the cell is possible by 2 methods. The first one—the cells, which have a membrane bound alpha subunit of the receptor, are bound to interleukin-6 to the receptor already assembled from the alpha subunit and gp130 molecules. The second one—the cells, which have only gp130 on the membrane, are bound to a complex of interleukin-6 with a soluble form of the alpha subunit. On the cell membrane, the complete complex is assembled and then the cell reaction cascade is initiated. Blocking the effect of cytokine and, therefore, inflammatory reaction may be achieved by preventing the complete assembly of the receptor consisting of the alpha-subunit and gp130 molecules, and interleukin-6. With specific antibodies bound with one of the molecules, the complete complex assembly is prevented, thus blocking the signal transduction inside the cell.

Polypeptides specifically bound to IL-6 (see Patent No. 2550262 of the Russian Federation), IL-6R or gp130 indicate a significant inhibiting influence on IL-6 performance. Medicinal products based on an antibody (tocilizumab) which binds to IL-6R and blocking its interaction with IL-6 are widely used in treatment of rheumatoid arthritis and systemic juvenile idiopathic arthritis both in the form of monotherapy, and in combination with methotrexat and/or other basic anti-inflammatory drugs.

The provided data allow to assume that the development of a product based on an anti-IL-6R antibody will allow to provide full coverage treatment of patient with this disease.

Receptor IL-6 (IL-6R, IL6R, CD126) is a complex of molecules, initiating the cell response cascade when activated, resulting in active synthesis of proteins involved in further inflammatory response reactions. The receptor is activated during binding of IL-6 to the receptor alpha unit having a mass of 80 kDa, which prevents signal transduction, and two gp130 molecules having a mass of 130 kDa, which transduce a signal inside the cell (SimonA.JonesTheFASEBJournal 15(1):43-58). There are two forms of the α-receptor as follows: a membrane-bound form (mIL-6R) and soluble form (sIL-6R 38 kDa). The soluble form is produced as a result of transmembrane proteolysis or alternative splicing of mIL-6R mRNA. The soluble form of IL-6sR allows cells to response to cytokine which lack mIL-6R on the membrane surface.

Blocking IL-6 signal with polypeptides which bind to the receptor has a number of advantages over those being directly bound to IL-6. Thus, antibodies against IL-6 bind to both the target intra-articular ligand, and IL-6 circulating in blood. Whereas antibodies bound to IL-6R influence in both cells comprising mIL-6R on the surface and cells comprising only gp130.

SUMMARY OF THE INVENTION

1. Definitions

Unless defined otherwise, all technical and scientific terms used herein have the same meaning as is commonly understood by one of ordinary skill in the art. Although methods and materials similar or equivalent to those described herein can be used in the practice or testing of embodiments of the invention, exemplary methods and/or materials are described below. All publications and other references mentioned herein are incorporated by reference in their entirety. In case of contradiction, this description, including definitions, shall prevail. Although a number of prior art publications are referred to herein, such reference does not constitute an admission that any of these documents form part of the common general knowledge in the art.

Further, unless otherwise required by context, singular terms shall include pluralities and plural terms shall include the singular. Typically, the classification and methods of cell and tissue culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's instructions, as is common in the art, or as described herein.

Throughout this disclosure and embodiments, the word "have" and "comprise" or variations thereof, such as "has" or "having", "comprises" or "comprising" shall be understood to imply the inclusion of a stated integer or group of integers but not the exclusion of any other integer or group of integers.

Unless otherwise indicated, amino acids are represented by their single letter code.

As used herein, the terms "Interleukin-6", "IL6", and "IL-6" are interchangeable.

The term "IL-6R", "IL6R" or CD126 refers to an interleukin-6 receptor.

The term "sIL-6R" refers to a soluble form of a receptor of interleukin-6.

The term "mIL-6R" refers to a membrane-bound receptor of interleukin-6.

The term "antibody" and "immunoglobulin" are interchangeable and refer to a full-size antibody in that form they are synthesized by cells of the immune system or other organisms having been genetically engineered.

Full-size antibodies are composed of four polypeptide chains:

two heavy chains (H) (approximately 50-70 kD at full length) and two light chains (L) (approximately 25 kD at full length) bound to each other with disulfide bridges.

The N-terminus (amino terminal part) of each chain includes a variable region of about 100-110 or more amino acids which are basically responsible for antigen recognition.

C-terminus (carboxy-terminal) part of each chain determines a constant region, basically responsible for a function of an effector.

Variable regions of heavy and light chains form an antigen-binding center (or region).

Light chains of antibodies are classified as kappa or lambda, each of which has a particular constant region. Each light chain is composed of a variable region of N-terminal part of light chain ("LCVR" or "VL") and a constant region of light chain consisting of one CL domain.

Heavy chains are classified as gamma, mu, alfa, delta or epsilon; they determine the antibody isotype such as IgG, IgM, IgA, IgD and IgE respectively, and several of them can be further divided into subclasses (isotypes), for example IgG1, IgG2, IgG3, IgG4, IgA1 and IgA2. Each type of heavy chain can be characterized with a constant region—Fc. Each heavy chain is composed of a variable region of N-terminal heavy chain ("HCVR" or "VH") and a constant region of heavy chain CH. A constant region of heavy chain is composed of three domains (CH1, CH2 and CH3) for IgG, IgD and IgA, and 4 domains (CH1, CH2, CH3 and CH4) for IgM and IgE.

The HCVR and LCVR regions can be additionally subdivided into regions of hypervariability, termed Rf-hypervariable regions (CDR), interspersed with more conservative regions, termed framework regions (FR).

Each HCVR and LCVR is composed of three CDRs and four FRs, arranged from amino-terminus to carboxy-terminus in the following order: FR1, CDR1, FR2, CDR2, FR3, CDR3, FR4.

CDRs comprise the majority of residues, which specifically interact with antigen.

Variable regions of each pair light/heavy chain form antibody-antigen binding sites. As used in this application, an "antigen-binding part", or "antigen-binding region", or "antigen-binding domain" or "antigen-binding center" interchangeably relate to such part of a antibody molecule comprising amino acid residues which interact with an antigen and give the antibody specificity and affinity in relation to the antigen. This part of an antibody includes "framework" amino acid residues needed to maintain appropriate conformation of antigen-binding residues.

The term "antibody" in this application not necessarily refers to a human antibody, this may be a rodent antibody, an antibody of animal of the order Primates or Camelidae; preferably an antibody of a mouse, macaque; an antibody of a camel or a lama; a chimeric antibody, humanized antibody or fully human antibody.

The term "antibody" in this context also embraces artificial single-chain antibodies having a structure close to the structure of natural antibodies.

Said antibodies may be either glycolised or free from polysaccharide residues.

An antibody of the present invention may be understood as a monoclonal antibody. The term "monoclonal antibody", as used herein, refers to a homogenous or substantially homogeneous antibody population (i.e. at least about 89%, 90%, 91%, 92%, 93%, 94%, 95%, 96%, more preferably at least about 97% or 98%, or even more preferably at least 99% of antibodies in the population will compete in ELISA for the same antigen/epitope, or even further preferably antibodies are identical in their amino acid sequence).

Also monoclonal antibodies may be understood as antibodies having identical or substantially identical amino acid sequence, though they may differ by post-translational modification, for example glycosylation pattern.

Monoclonal antibodies of the invention may be obtained using, for example, the hybridoma techniques well known in the art, as well as recombinant techniques, phage display techniques, synthetic techniques or a combination of such techniques or other techniques well known in the art.

However, the term "monoclonal antibody" is not limited to antibodies obtained solely by the hybridoma technique. This term may refer to an antibody, obtained from a single copy or a clone, including, for example, any eukaryotic, prokaryotic or phage clone.

Amino acid residues in this text are numbered with a reference to a reference antibody which means an antibody heavy chains of which have the sequence SEQIDNO:10, and light chains—the sequence SEQIDNO:9. In all other cases CDR amino acid residues within the limits of HCVR and LCVR antibody regions are numbered and positioned in accordance with Kabat et al., Sequences of Proteins of Immunological Interest, 5th Ed. Public Health Service, National Institutes of Health, Bethesda, Md. (1991), unless otherwise indicated.

According to the invention antibodies may be obtained by different design techniques, including the use of recombinant methods, including shuffling of DNA obtained from different sources.

Antibodies of the present invention may be mono-specific, bi-specific and multi-specific. Multi-specific antibodies may be specific in relation to various epitopes of one target polypeptide or may comprise antigen-binding domains, specific in relation to the other or several antigens, apart from IL-6R or to various IL-6R epitopes (see, for example, Tuttetal. (1991) J. Immunol. 147:60-69).

Bindings among antigen-binding parts of mono-, bi- and multi-specific antibodies may vary. In particular, bindings among antigen-binding parts may be chemical; or different antigen binding parts may be bound through a common polypeptide chain; or by noncovalent association of different chains with each other; or antigen-binding parts may be combined with each other by means of other antibody or antibody fragment.

The term "anti-sIL-6R-antibody", "antibody to sIL-6R", "antibody specifically bound to a interleukin-6 receptor", etc. are interchangeable in the context of this application and refer to an antibody, which is specifically bound to a IL-6 receptor. The term "mIL-6R" refers to a membrane-bound receptor of interleukin-6.

The term "sIL-6R" refers to a soluble form of a receptor of interleukin-6.

The term "antibody fragment" refers to any fragment of a natural and artificially designed antibody, which comprises three CDRs of a heavy and three CDRs of a light chain. The antibody fragment may be assumed as, in particular, substantially full-size antibody with a shortened framework region of a heavy chain, full or full-size Fc-region, part or fragment of an antibody comprising an antigen-binding part, for example, Fab-fragment, Fab'-fragment or F(ab')2-fragment of an antibody, scFv, (scFv)2, dsFv, single-chain Fv-fragment which may be obtained by binding of DNA, encoding LCVR and HCVR with a linker sequence (see. Pluckthun, The Pharmacology of Monoclonal Antibodies, vol. 113, Rosenburg and Moore eds., Springer-Verlag, New York, p. 269-315, 1994).

The term "antibody fragment" must not be understood as one indicating the origin of a full-size antibody. The "antibody fragment" may be obtained absolutely irrespective of full-size antibodies by any known method.

Also, the "antibody fragment" may be assumed as an artificially designed polypeptide or a product comprising peptide and non-peptide parts, if the antibody fragment comprises said three or less CDRs of a heavy and three or less CDRs of a light chain, placed so that polypeptide or said product retain capability of specific or preferential binding of their target (for example, an epitope or an antigen).

All the rest said above in relation to antibodies, including that associated with glycosylation is also applicable to antibody fragments, if it is compatible with a common sense.

The term "specifically binds" as used in this application refers to the situation when one region of the specifically bound pair does not bind to a large degree molecules different from its specific binding partner (partners). The term is also applicable where e.g. an antigen-binding domain of an antibody of the invention is specific for a particular epitope that is carried by a number of antigens; in this case, the specific antibody comprising the antigen-binding domain will be able to specifically bind to various antigens carrying the epitope. Thus, an antibody of the invention or its fragment specifically binds a human sIL-6R, whereas it almost cannot be bound to human proteins IL12, IL23, EGFR, CD3, IGFR, CTGF, FGF2, PD1, PSCK9, CD38, GCSF, interferon alfa-2b.

The term "epitope" refers to that part of a molecule, which can be recognized and bound to an antibody in one or more antigen-binding regions of an antibody. Epitopes often consist of a chemically active surface grouping of molecules such as amino acids or sugar side chains and have specific three-dimensional structural characteristics as well as specific charge characteristics. An "inhibiting epitope" and/or "neutralizing epitope" is assumed an epitope which in the context of an intact antigen molecule and when being bound to an antibody specific to the epitope results in loss of or decrease in biological activity of a molecule or an organism which comprises a molecule in vivo or in vitro. The term "epitope" as used in this application, besides that, relates to a part of a polypeptide that initiates antigenic and/or immunogenic activity in an animal, preferably a mammal, for example a mouse or a human. The term "antigenic epitope" as used herein is a polypeptide fragment which can specifically bind the antibody and can be detected by any technique well known from the prior art, for example, by the standard immunoassay. Antigen epitopes are not necessarily immunogenic, however, they can be immunogenic. "Immunogenic epitope" as used herein is defined as a polypeptide fragment that evokes an antibody response in animals, as determined by any method known from the prior art. "Non-linear epitope" or "conformational epitope" comprise non-adjacent polypeptides (or amino acids) within an antigen protein that binds to epitope-specific antibody.

The phrase "biological property", or the term "activity" or "bioactivity" in reference to an antibody of the present invention, are used interchangeably herein and include, but are not limited to, epitope/antigen affinity and specificity for sIL-6R, ability to antagonize IL-6, the stability of an antibody and immunogenic properties of an antibody in vivo. Other identifiable biological properties of an antibody include, for example, cross-reactivity, (i.e., with non-human homologs of a target peptide, or with other proteins or targets, generally), and ability to preserve high levels of expression of protein in mammalian cells. The abovementioned properties and characteristics may be observed, measured or assessed by techniques recognized in the art, including, but not limited to, ELISA assay, competitive ELISA assay, or KINEXA surface plasmon resonance analysis, neutralization analyses in vitro or in vivo without limitations, receptor binding, production and/or secreting of cytokine or growth factor, signal transduction and immunohistochemistry of tissue slices obtained from different sources, including humans, primates or any other source.

The term "inhibit" or "neutralize" as used in this application in relation to the activity of antibody of the invention refers to an ability to substantially hold back, restrain, prevent, limit, slow down, abort, destroy, stop, decrease or convert, for example, development or severity of the thing which is inhibited, including, but not limited to the abovementioned, biological activity (for example, IL-6 activity) or property, disease or condition. Inhibition or neutralization of IL-6 activity as a result of binding antibody of the invention to sIL-6R amounts to preferably at least approximately 20, 30, 40, 50, 60, 70, 80, 90, 95% or more.

The term "patient" in this application relates to a mammal, including, but not limited to said, mice, monkeys, humans, agricultural mammals, sports mammals and pet mammals; the term preferably relates to humans. In a certain embodiment, a patient, preferably a mammal, preferably a human, can be additionally characterized by a disease or disorder, or condition mediated by IL-6, which may be improved by decreasing biological activity of IL-6.

The term "vector" includes a nucleic acid molecule capable of transporting another nucleic acid which it is bound to, including plasmids and viral vectors, but not limited thereto. Certain vectors are able to autonomously replicate each other in a host cell where they were injected, whereas the other vectors may be integrated into a host cell genome thus being replicated along with a host genome. Moreover, certain vectors are capable of directing gene expression to which they are functionally bound. Such vectors are termed in this application "recombinant expression vectors" (or, simply "expression vectors"), and illustrative vectors are well known in the art.

As used in this application expressions "cell", "host cell", "cell line" and "cell culture", "cell line as a producer" are used as interchangeable and include an individual cell or cell culture being a recipient of any separated polynucleotide of the invention or any recombinant vector (any recombinant vectors) which comprise a sequence coding HCVR, LCVR or a monoclonal antibody of the invention. Host cells include individual cell's offspring, and the offspring not necessarily may be fully identical (by morphology or complete DNA complement) to an original parent cell due to natural, accidental or intentional mutations and/or changes. A host cell includes cells transformed, transduced or infected with a recombinant vector, or a monoclonal antibody which expresses a polynucleotide of the invention or its light or heavy chain. A host cell, which comprises a recombinant vector of the invention (both being consistently integrated into a host chromosome, and not being integrated) may also be termed a "recombinant host cell". Preferable host cells for use in the invention are CHO cells (for example, ATCC CRL-9096), NSO cells, SP2/0 cells, COS cells (ATCC, for example, CRL-1650, CRL-1651), and HeLa (ATCC CCL-2). Additional host cells for use in the invention include plant cells, yeast cells, other mammalian cells and prokaryotic cell.

The term "affinity" is intended to refer to measuring the attraction between an antigen and binding molecule, e.g., an antibody. The intrinsic ability to attract a binding molecule for an antigen is typically expressed as the binding affinity equilibrium constant (KD) of a particular binding molecule-antigen interaction. A binding molecule is said to specifically bind to an antigen when KD is <1 mM, preferably <100 nM. A KD binding affinity constant can be measured, e.g., by surface plasmon resonance (BIAcore™) or bio-layer interferometry, for example using ProteOn™ XPR36 SPR (Bio-Rad) or Octet™ systems.

The term "Ka" as used herein is intended to refer to the association rate of a particular antibody-antigen interaction, whereas the term "Kd" is intended to refer to the dissociation rate of a particular antibody-antigen interaction. The term "KD" as used herein is intended to refer to the affinity constant, which is obtained from the ratio of Kd to Ka (i.e. Kd/Ka) and is expressed as a molar concentration (M). KD values for antibodies can be determined using methods well established in the art.

A preferred method for determining the KD of an antibody is surface plasmon resonance, preferably using a biosensor system such as a Biacore® system.

As used herein, the term "high affinity" for an IgG antibody is intended to refer to an antibody having KD-E-10-E-08 M, more preferably E-10-E-09 M or less and even more preferably E-10 M or less for a target antigen. However, "high affinity" binding can vary for other antigen isotypes. For example, "high affinity" binding for an IgM isotype refers to an antibody having KD E-10-E-07 M or less, more preferably E-10-E-08 M, or even more preferably E-10-E-09 M or less.

The term "$k_{off}$" as used herein is intended to refer to the dissociation rate constant of a particular binding molecule-antigen interaction. The dissociation rate constant (koff+) can be measured using bio-layer interferometry, for example, using Octet™ system.

The term "epitope" as used herein is intended to refer to a portion (determinant) of an antigen that specifically binds to a binding molecule (for example, an antibody or a related molecule, such as a bispecific binding molecule). Epitope determinants usually consist of molecules such as amino acids or carbohydrates or sugar side chains and typically comprise specific three dimensional structural characteristics, as well as specific charge characteristics. Epitopes can be either "linear" or "conformational". In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope of an antigen is determined, it is possible to generate antibodies to that epitope using techniques well known in the art. In addition, genera-tion and characterization of antibodies or other binding molecules may elucidate information about desirable epitopes. From this information, it is then possible to competitively screen antibodies for binding to the same or identical epitopes, e.g., by conducting competition studies to find binding molecules that compete with one another for binding to the antigen. The term "epitope" as used in this application, besides that, relates to a part of a polypeptide that initiates antigenic and/or immunogenic activity in an animal, preferably a mammal, for example a mouse or a human. The term "antigenic epitope" as used herein is a polypeptide fragment which can specifically bind the antibody and can be detected by any technique well known from the prior art, for example, by the standard immunoassay.

One can determine whether an antibody or other binding molecule binds to the same epitope or cross-competes for binding with an IL-6 binding molecule of the present invention by using methods known in the art. In one embodiment, one allows a molecule of the invention to bind to IL-6 under saturating conditions and then measures the ability of the test antibody to bind to said target antigen. If the test antibody is able to bind to the target antigen at the same time as a reference binding molecule, then the test antibody binds to a different epitope than that of the reference binding molecule. However, if the test antibody is not able to bind to the target antigen at the same time, then the test antibody binds to the same epitope, an overlapping epitope, or an epitope that is in close proximity to the epitope bound to the binding molecule. This experiment can be performed using ELISA, RIA, BIACORE™, bio-layer interferometry or flow cytometry. To test whether a binding molecule of the invention cross-competes with another binding molecule, one may use the competition method described above in two directions, i.e. determining if the known binding molecule blocks the test binding molecule and vice versa. Such cross-competition experiments may be performed, e.g., using IBIS MX96 SPR or Octet™ system.

In one embodiment, a binding molecule of the invention is a monoclonal antibody. As used herein, the acronym "mAb" is intended to refer to a monoclonal antibody, i.e. an antibody synthesized and isolated by a separate clonal population of cells. A clonal population can be a clonal population of immortalized cells. In some embodiments, the immortalized cells in a clonal population are hybrid cells—hybridomas—typically produced by the fusion of individual B lymphocytes from immunized animals with individual cells from a lymphocytic tumour. Hybridomas are a type of constructed cells and do not exist in nature.

The class (isotype) and subclass of antibodies can be determined by any method known in the art. In general, the class and subclass of an antibody can be determined by antibodies specific to a certain class and subclass of antibodies. Such antibodies are commercially available. The class and subclass can be determined using ELISA, western blot analysis, and other methods. In another embodiment, the class and subclass can be determined by virtue of sequencing all or part of the heavy and/or light chain constant domains of antibodies, comparing amino acid sequences thereof with known amino acid sequences of various classes and subclasses of immunoglobulins, and determining the class and subclass of antibodies.

The term "identity" or "homology" in the context of nucleic acid sequences is intended to refer to the residues in two sequences which are the same when aligned for maximum correspondence. Comparison of sequence identity may extend over a length of at least about nine nucleotides, commonly at least about 18 nucleotides, more commonly at least about 24 nucleotides, typically at least about 28 nucleotides, more typically at least about 32 nucleotides, and preferably at least about 36, 48 or more nucleotides. There are a number of various algorithms known in the art which can be used to measure nucleotide sequence identity. For example, polynucleotide sequences can be compared using FASTA, Gap or BESTFIT, which are programs in Wisconsin Package Version 10.0, Genetics Computer Group (GCG), Madison, Wisconsin FASTA, which includes, e.g., FASTA2 and FASTA3 programs, provides alignments and percent sequence identity of the regions of the best overlap between the query and search sequences (Pearson, Methods Enzymol. 183:63 98 (1990); Pearson, Methods Mol. Biol. 132: 185-219 (2000); Pearson, Methods Enzymol. 266: 227-258 (1996); Pearson, J. Mol. Biol. 276: 71-84 (1998)). Unless otherwise specified, default parameters for a particular program or algorithm are used. For instance, percent sequence identity between nucleic acid sequences can be determined using FASTA with default parameters (word size of 6 and NOPAM factor for the scoring matrix) or using Gap with default parameters as provided in GCG Version 6.1.

The term "homologous" with regard to a polypeptide sequence of an antibody should be construed as an antibody exhibiting at least 70%, preferably 80%, more preferably 90% and most preferably 95% sequence identity relative to a polypeptide sequence. The term in relation to a nucleic acid sequence should be construed as a sequence of nucleotides exhibiting at least 85%, preferably 90%, more preferably 95% and most preferably 97% sequence identity relative to a nucleic acid sequence.

The term "bispecific antibody" or "multispecific antibody" includes an antibody capable of selectively binding two or more epitopes. Bispecific antibodies, e.g., may comprise two different antigen-binding portions, wherein said antigen-binding portions specifically bind different epitopes either on different molecules (e.g., antigens), or on the same molecule (e.g., on the same antigen). If a bispecific antibody is able to selectively bind two different epitopes (a first epitope and second epitope), the affinity of the first antigen-binding portion for the first epitope will typically be at least one to two, or three, or four orders of magnitude lower than that of the first antigen-binding portion for the second epitope, and vice versa. Epitopes recognized by a bispecific antibody may be the same or different targets (e.g., on the same or a different protein). Bispecific antibodies can be prepared, for example, by combining heavy chains that recognize different epitopes on the same antigen. For example, nucleic acid sequences encoding variable heavy chain sequences that recognize different epitopes may be fused to nucleic acid sequences encoding various heavy chain constant regions, and such sequences may be expressed in a cell which expresses an immunoglobulin light chain. A typical bispecific antibody comprises two heavy chains, each comprising three heavy chain CDRs followed (from N-terminus to C-terminus) by a CH1 domain, hinge region, CH2 domain and CH3 domain, and immunoglobulin light chain which either does not have antigen-binding specificity but is able to combine with each of the heavy chains, or is able to combine with each of the heavy chains and bind one or more epitopes restricted by antigen-binding heavy chain regions, or is able to combine with each of the heavy chains and promotes binding of one or the both heavy chains to one or the both epitopes.

2. Object

The object of this invention is to create alternative antibodies or their fragments having ability to specifically bind to a human interleukin-6 receptor, which would be applied as a medicinal product for treatment or diagnosis of diseases or to relief symptoms mediated by interleukin-6.

3. Antibodies of the Invention and their Fragments

According to this invention there is provided an antibody or antigen-binding fragment thereof in which an ability to bind to a human interleukin-6 (IL-6) receptor is ensured due to that it includes an amino acid sequence that is at least 75% homologous to the sequence of SEQ ID NO: 3.

In one embodiment, the present invention relates to an antibody or fragment thereof which comprise the amino acid sequence of SEQ ID NO: 3.

In some embodiments, the present invention relates to an antibody or fragment thereof which contains:
    a sequence of a heavy chain variable domain that is at least 75% homologous to the sequence of SEQ ID NO:9, and
    a sequence of a light chain variable domain that is at least 75% homologous to the sequence of SEQ ID NO:10.

In one embodiment, the present invention relates to an antibody or fragment thereof which comprise the amino acid sequences of SEQ ID NO: 1-3.

In some embodiments, a binding fragment competes for binding or binds to the same epitope as a binding domain comprising the amino acid sequence of SEQ ID NO: 7.

In some embodiments, a binding fragment is at least 90% homologous to the amino acid sequence of SEQ ID NO: 7. In one embodiment of the invention, a binding domain comprises the amino acid sequence of SEQ ID NO: 7.

In some embodiments of the invention, an antibody or antigen-binding fragment thereof is characterized in that it relates to human IgG1, IgG2, IgG3, IgG4 isotypes.

In some embodiments, an antibody or fragment thereof has a heavy chain sequence that is at least 90% homologous to the sequence of SEQ ID NO: 9.

In some embodiments, an antibody or fragment thereof has a light chain sequence that is at least 90% homologous to the sequence of SEQ ID NO: 10.

In some embodiments, the Fc constant region of IgG1 isotype comprises E233P, L234A, L235A, E236P, L237V and/or L238A mutations.

In some embodiments, the Fc constant region of IgG1 isotype comprises mutations that increase animal or human pharmacokinetic parameters, such as $t_{1/2\beta}$ (h) or $C_{max}$ (µg/ml).

In some embodiments, the Fc constant region of IgG1 isotype comprises M255Y, S257T and/or T259E mutations that increase animal or human pharmacokinetic parameters, such as t½β (h) or Cmax (µg/ml).

In some embodiments, an antibody or antigen-binding fragment thereof have at least one of the following properties:
    a) has such aggregation stability that the aggregate content does not increase by more than 5% of the initial content in solution at concentrations above 10 mg/ml and at a storage temperature of T=4° C. for more than 6 months;
    b) has such aggregation stability that the aggregate content does not increase by more than 5% of the initial content in solution at concentrations above 10 mg/ml and with an increase in temperature to 37° C. for more than 2 weeks;
    c) has such aggregation stability that the aggregate content does not increase by more than 5% of the initial content in solution at concentrations above 10 mg/ml and with an increase in temperature to 50° C. for more than 24 hours;

d) has a dissociation constant KD of not more than $10^{-9}$ (M) when binding to human IL-6 receptor;

e) has a kinetic association constant kon (1/Ms) of at least $10^5$ (1/Ms) when binding to human IL-6 receptor;

f) has a kinetic dissociation constant dis (1/s) of not more than $10^4$ (1/s) when binding to human IL-6 receptor;

g) demonstrates an antiproliferative activity on a culture of interleukin-6 dependent DS1 cells with a rated value IC50 not exceeding $10^{-8}$ M;

h) demonstrates blocking of STAT-3 signaling on a culture of interleukin-6 dependent cells with a rated value IC50 not exceeding $10^{-8}$ nM.

3. Bispecific Antibodies According to the Invention

According to the present invention there is also provided a bispecific antibody comprising an antigen-binding fragment of the abovementioned antibody.

An example of such antibody may a bispecific antibody comprising antigen-binding parts, CDRs of which differ from each other and have a total homology over than 95% in relation to each other.

4. DNA

According to the present invention there is also provided DNA intended for obtaining of the abovementioned antibody or antigen-binding fragment thereof which includes sequences which are consistent with said CDRs.

5. Expression Vector

According to the present invention there is also provided an expression vector comprising one or several said DNAs.

For the expression there may be used systems, described in Section 6.2 "NUCLEIC ACIDS AND EXPRESSION SYSTEMS" of the international publication WO 2010/148223 (see the analogue—Patent of the Russian Federation 2567639).

6. Cell Line

According to the present invention there is also provided a cell line comprising said vector or said DNA in cells.

7. A Method of Obtaining an Antibody

According to the present invention there is provided a method of obtaining said antibody or antigen-binding fragment thereof, which comprises culturing of said cell line in a culture medium under conditions sufficient to obtain said antibody or antigen-binding fragment thereof, with the following isolating and purifying of the obtained antibody or antigen-binding fragment thereof.

8. Pharmaceutical Composition

According to the present invention there is provided a pharmaceutical composition for treatment of a disease or condition associated with the effect of interleukin-6 (IL-6), or for removing or relief of a symptom associated with an undesirable effect of IL-6, comprising an effective amount of an antibody or antigen-binding fragment thereof according to claim 1 or according to any of claims dependent on claim 1, in combination with one or several pharmaceutically acceptable excipients, diluents or carriers.

It is preferable when a composition according to the claim represents parenteral solution.

Alternatively, a composition according to the claim may represent lyophilized powder.

The composition according to the claim may be used in therapy and/or diagnosis of a disease selected from the following group of diseases or disorders: rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, atopic dermatitis, scleroderma, graft versus host disease, organ transplant rejection, acute or chronic immune disease associated with organ transplantation, sarcoidosis, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, adult (acute) respiratory distress syndrome, alopecia, alopecia greata, seronegative arthropathy, arthropathy, Reiter's disease, psoriatic arthropathy, ulcerative colitic arthropathy, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, arteritis, primary sclerosing hepatitis, cryptogenic autoimmune hepatitis, cryptogenic fibrosing alveolitis, post-inflammatory interstitial lung disease, interstitial pneumonitis, chronic eosinophilic pneumonia, postinfectious interstitial lung disease, gouty arthritis, autoimmune hepatitis, type-1 autoimmune hepatitis (classical autoimmune or lupoid hepatitis), type-2 autoimmune hepatitis, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic scleroderma, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver disease, allergy and asthma, mental disorders (including depression and schizophrenia), Th2 Type and Th1 Type mediated diseases, conjunctivitis, allergic contact dermatitis, allergic rhinitis, alpha-1-antitrypsin deficiency, amyotrophic lateral sclerosis, anemia, cystic fibrosis, cytokine therapy associated disorders, demyelinating diseases, dermatitis, iridocyclitis, uveitis, optic neuritis, ischemia-reperfusion injury, ischemic stroke, juvenile rheumatoid arthritis, autoimmune enteropathy, autoimmune hearing loss, autoimmune lymphoproliferative syndrome (ALPS), autoimmune myocarditis, autoimmune premature ovarian failure, and blepharitis.

Antibodies of the invention may be administered individually or in combination with a pharmaceutically acceptable carrier, diluent and/or filler as a single or multiple doses. Pharmaceutical compositions for administration have been developed so as to comply with the selected administration regimen, and pharmaceutically acceptable diluents, carriers and/or fillers such as dispersing agents, buffers, surface-active agents, preservation agents, solubilizing agents, isotonic agents, stabilization agents, cryoprotectors have been selected taking into account an appropriate dosage form for the composition. Said compositions have been developed in compliance with traditional techniques specified in, for example, Remington, The Science and Practice of Pharmacy, 19th Edition, Gennaro, Ed., Mack Publishing Co., Easton, PA 1995, wherein different techniques of obtaining formulations known to those skilled in the art in general are described.

A pharmaceutical composition comprising an antibody or fragment thereof of the invention may be administered to a patient using standard routes of administration, including peroral, intravenous, intraperitoneal, subcutaneous, pulmonary, transdermal, intramuscular, intranasal, buccal, sublingual, and suppository.

A pharmaceutical composition of the invention comprises an effective amount of an antibody of the invention. An "effective amount" is the amount which is effective at doses and within time periods necessary to achieve a desirable therapeutic result. A therapeutically effective amount of antibody may vary depending on such factors as condition of a disease, age, sex and weight of an individual, and the ability of an antibody or part of antibody to initiate a desirable reaction in the individual. An effective amount also represents the amount at which a therapeutically advantageous effect of an antibody prevails over a toxic or adverse effect. If an antibody is used for prophylactic purposes, than an "effective amount" is understood as the amount which is effective at doses and within time periods necessary to achieve a desirable prophylactic result. Since a prophylactic dose is used for individuals before or at the early stage of a disease, it is typical that the prophylactically effective amount may be less than the therapeutically effective amount.

An effective amount represents at least a minimum dose, but less than a toxic dose of an active agent necessary to ensure a therapeutic or prophylactic effect in a patient. On the other hand, an effective amount of an antibody of the invention represents amount which, in mammals, preferably humans, decreases biological activity of IL-6.

The route of administration of an antibody of the invention can be oral, parenteral, inhalation or local. Preferably antibodies of the invention can be involved in a pharmaceutical composition acceptable for parenteral administration. The term "parenteral" includes intravenous, intramuscular, subcutaneous, rectal, vaginal or intraperitoneal administration. Intravenous, intraperitoneal or subcutaneous injections are preferred routes of administration. Acceptable pharmaceutical carriers for such injections are well known from the prior art.

As described in appropriate guidelines, a pharmaceutical composition shall be sterile and stable under the conditions of production and storage in a container, which is provided by, for example, hermetically sealed vials (ampoules) or syringes. Thus, pharmaceutical compositions can be subjected to filtration sterilization after preparing the composition, or can be made microbiologically suitable by any other technique. A typical composition for an intravenous infusion can include 250-1000 ml of fluid such as sterile Ringer's solution, physiologic saline, dextrose solution or Hank's salt solution, and a therapeutically effective dose (for example, 1-100 mg/ml or more) of an antibody concentrate. A dose may vary depending on disease type and severity. It is well known from the state of medical art that doses for any of patients depend on multiple factors including patient's sizes, body surface area, age, specific compound to be administered, gender, duration and route of administration, general health state and other simultaneously administered medications. A typical dose can be, for example, in a range of 0.001-1000 µg; however, doses lower and higher than this illustrative range are anticipated, especially given the above-mentioned parameters. The daily parenteral dosing regimen may be from 0.1 µg/kg to 100 µg/kg of overall body weight, preferably from 0.3 µg/kg to 10 µg/kg, and more preferably from 1 µg/kg to 1 mg/kg, even more preferably from 0.5 to 10 mg/kg of body weight per day. The treatment process can be monitored by periodical assessment of patient's health state. For repeated administration for several days or longer, depending on patient's condition, the treatment is repeated until the desired response or suppression of symptoms of a disease. However, another dosing regimens not described herein can also be applied. The desired dose may be administered by single bolus or multiple bolus dosing, or by means of a continuous infusion of an antibody depending on a pharmacokinetic breakdown desired by a practitioner.

These suggested amounts of an antibody to a great extent depend on a decision of a therapeutist. The intended effect is the key factor for choosing a proper dose and regimen. Factors considered herein include a certain disease to be treated, a certain mammal to receive the treatment, clinical condition of a certain patient, disorder cause, antibody administration site, specific antibody type, route of administration, administration regimen and other factors well known in the medical arts.

Antibodies or fragments thereof may be frozen or lyophilizated and reconstituted before application in an appropriate sterile carrier. Lyophilization and reconstitution can result in some loss of antibody's activity. Dosages may have to be adjusted to compensate this loss. Generally, pH between 6 and 8 is preferred for a pharmaceutical composition.

9. Articles of Manufacture

In another embodiment of the invention it is provided an article of manufacture, comprising materials useful for treatment or prophylaxis of disorders or conditions described above.

The article of manufacture comprises a container with an antibody-containing pharmaceutical composition with a label, and possibly a package insert. Suitable containers include, e.g., vials, ampoules, syringes and analytical tubes. The containers may be made of a plurality of materials such as glass or polymer material. The container comprises a composition of the invention which is effective for treating an IL-6-mediated disease or disorder and can have a sterile access port (e.g., the container may be an intravenous solution bag or a vial having a stopper pierceable by a hypodermic injection needle). The active agent in a composition is anti-IL-6R-antibody of the invention. A label located on the container or a package insert attached thereto indicates that the composition is used for treating the desired disease. The article of manufacture may further comprise a second container with a pharmaceutically acceptable buffer such as phosphate-buffered saline, Ringer's solution and dextrose solution. It can further include other materials desirable from a commercial and consumer standpoint, including other buffers, diluents, filters, needles, syringes and package inserts.

10. Application

According to the present invention there is provided application of the abovementioned antibody or fragment thereof for the manufacture of a medicinal product.

It is preferable when said medicinal product is intended for use in therapy and/or diagnosis of diseases listed above as a prescription of a pharmaceutical composition.

Pathways a-d: Fermentas unstained marker, IL6R-H6 cell culture fluid before application on a column of 10 mcl, IL6R-H6F cell culture fluid after application on a column of 10 mcl, IL6R-H6F elution from 5 mcl.

Figure 2:
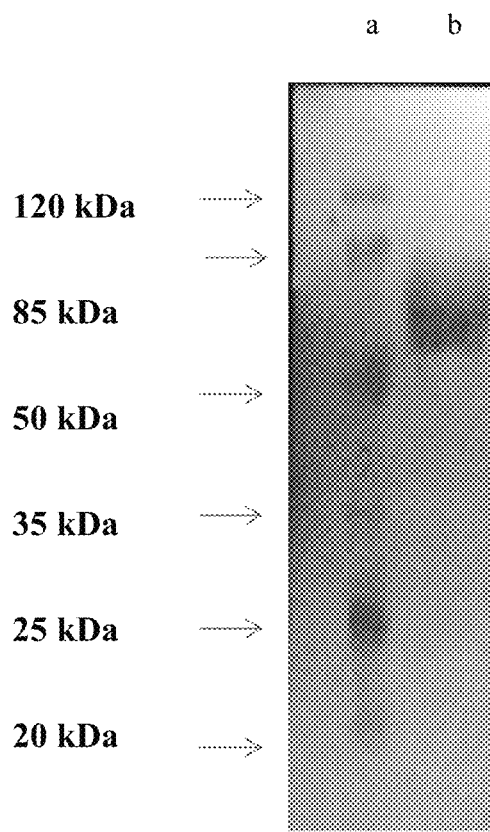

FIG. 2 is Western blot analysis of the cultured and purified human sIL-6R. After completion of gel electrophoresis under denaturing conditions of human sIL-6R in a 12% PAGE and its transfer into a membrane, binding to tocilizumab, and then anti-GoatahIgGIgG HRP was carried out. Staining was performed with DAB. Pathways a-d: Prestained marker, IL6R-flag-his 5 mcl.

Figure 3:
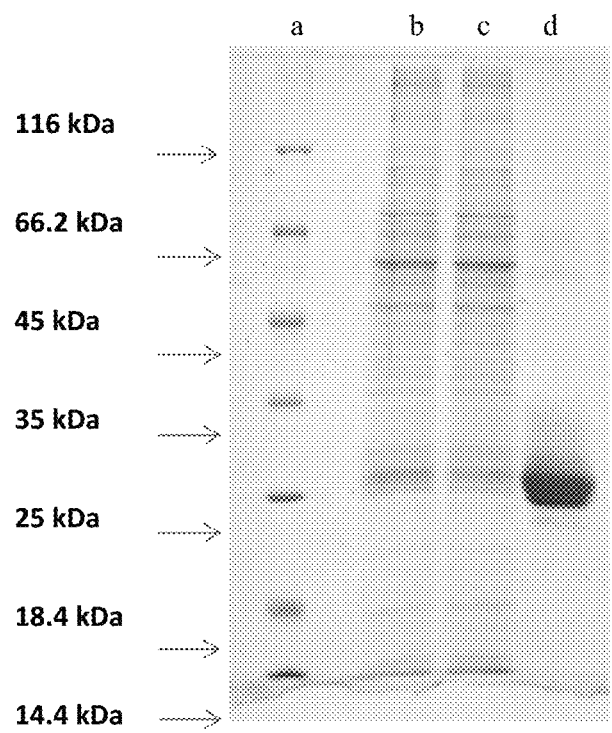

FIG. 3 is a gel electrophoresis under denaturing conditions of the cultured and purified human IL6-H6-EPEA (with 6 histidines and EPEA sequence on the protein C-terminus) in a 12% PAGE.

Pathways a-d: Fermentas unstained PW marker, IL6-H6-EPEA ccf before application on a 5 mcl column, IL6-H6-EPEA ccf after application a 5 mcl column, IL6-H6-EPEA elution from a 5 mcl column.

Figure 4:
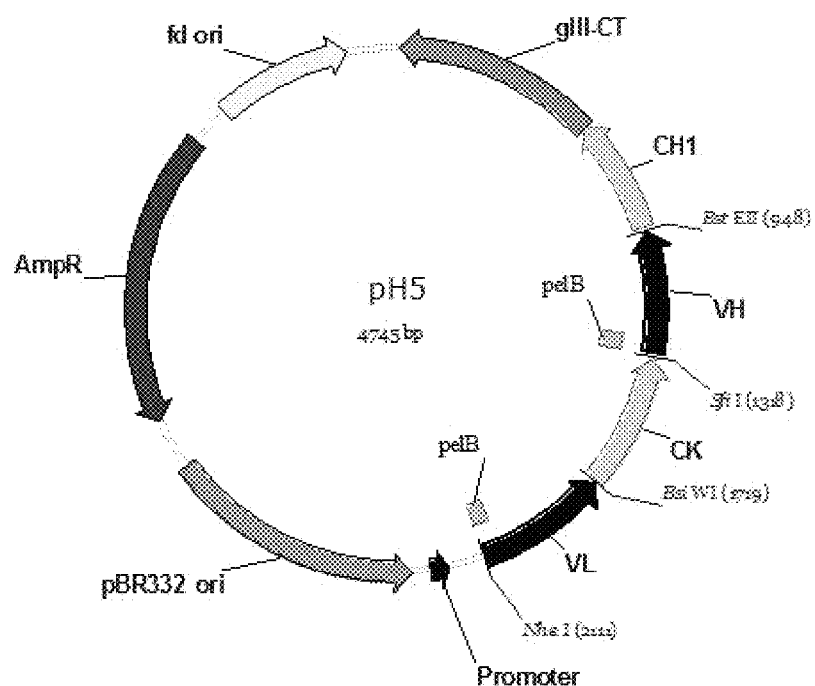

FIG. 4 are phagemid vectors for cloning Fab phage display libraries.

Figure 5:
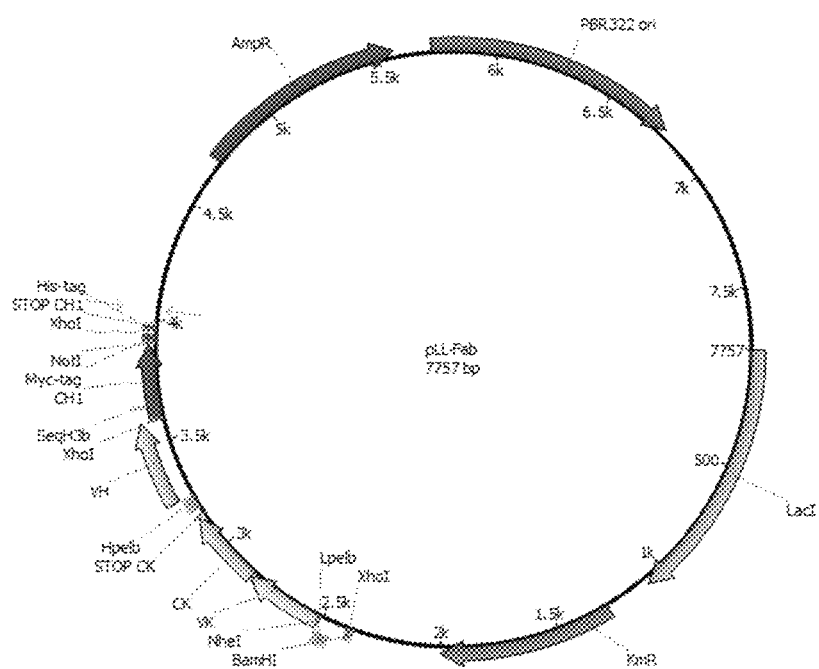

FIG. 5 is an expression plasmid for cloning and culturing of Fab.

Figure 6:
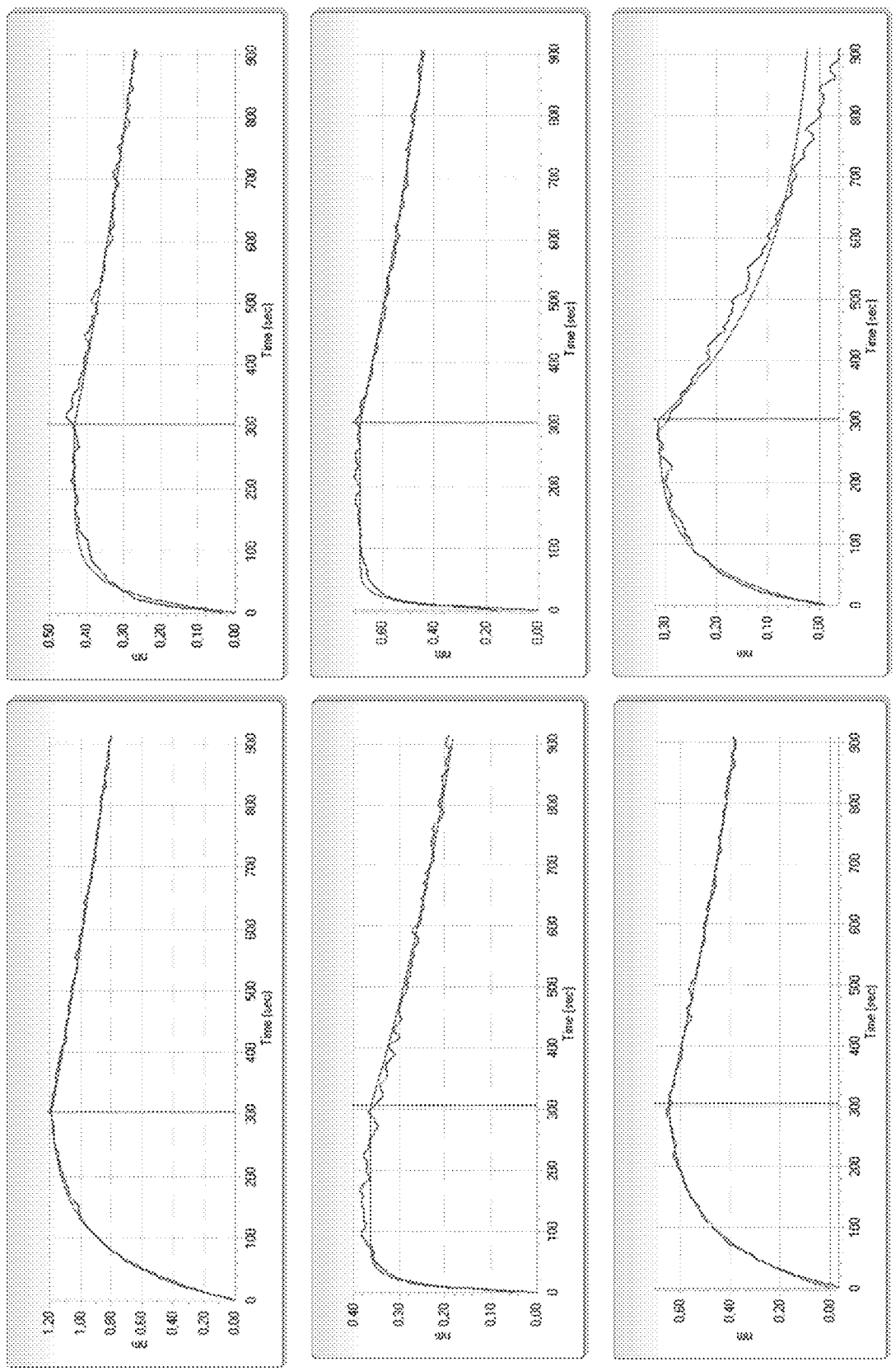

FIG. 6 are association and dissociation kinetics of Fab fragments with a human IL-6R alpha subunit using ForteBio.

Figure 7:
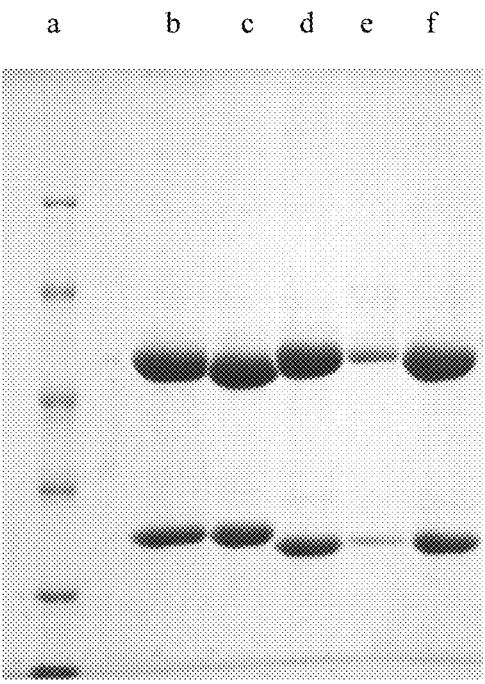

FIG. 7 is a gel electrophoresis under denaturing conditions of the cultured and purified full size antibodies of human IL-6sR in a 12% PAGE in the presence of beta-mercaptoethanol.

Pathways a-f: a—Fermentas unstained marker, b-f—anti-IL-6sR antibodies.

Figure 8:
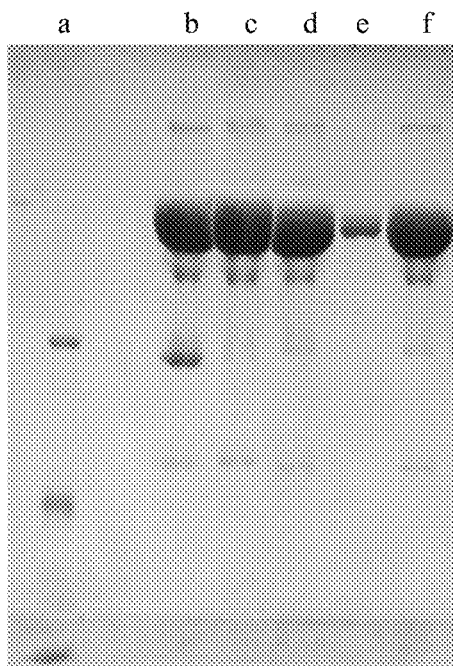

FIG. 8 is a gel electrophoresis under denaturing conditions of the cultured and purified full size antibodies of human IL-6sR in a 12% PAGE in the presence of beta-mercaptoethanol.

Pathways a-f: a—Fermentas unstained marker, b-f—anti-IL-6sR antibodies.

Figure 9:
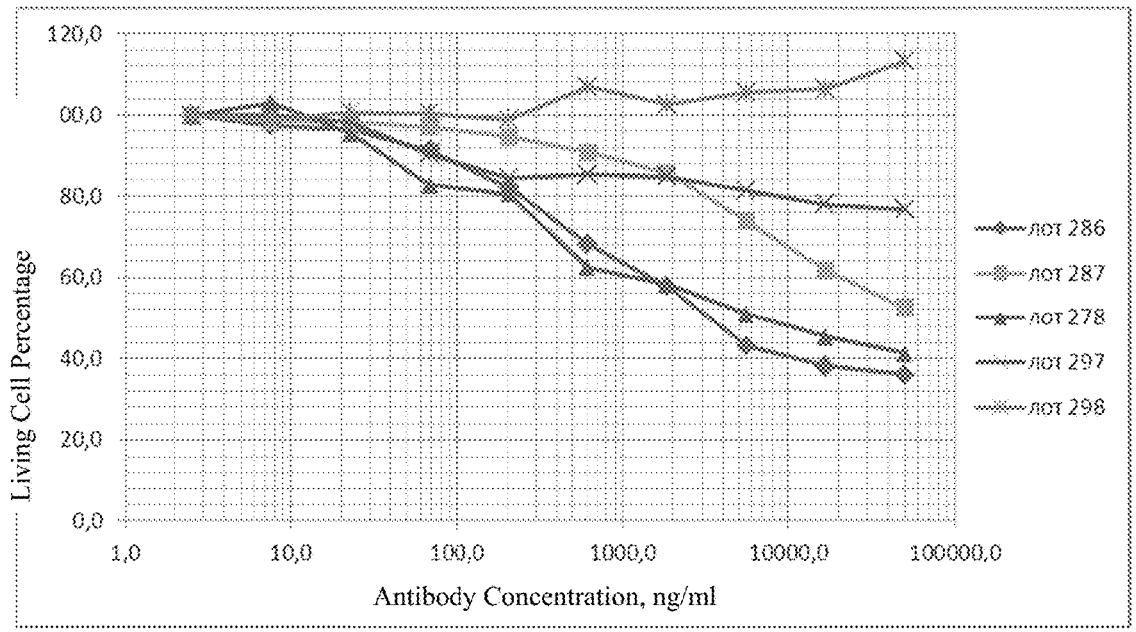

FIG. 9 is a cell inhibition test for DS-1 cell proliferation with anti-IL-6R antibodies.

Figure 10:
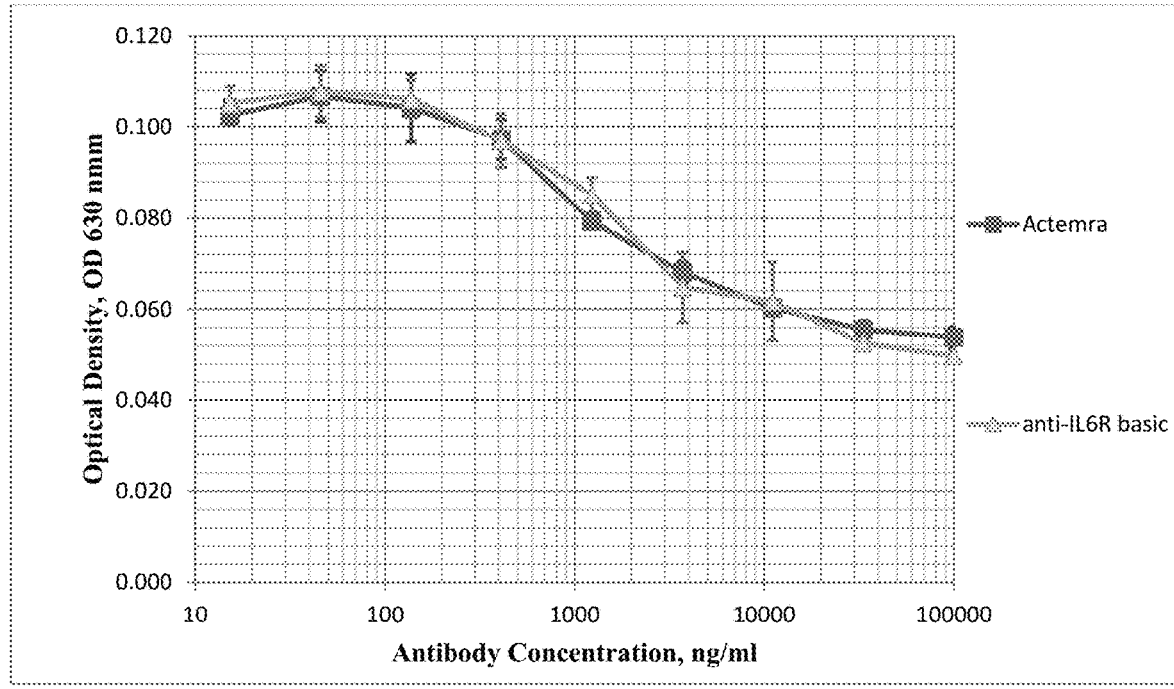

FIG. 10 is a cell test of STAT3 path inhibition analysis in HEK-Blue™ IL6 cell culture with BCD089 antibody (anti-IL-6sR) in comparison with tocilizumab.

Figure 11:
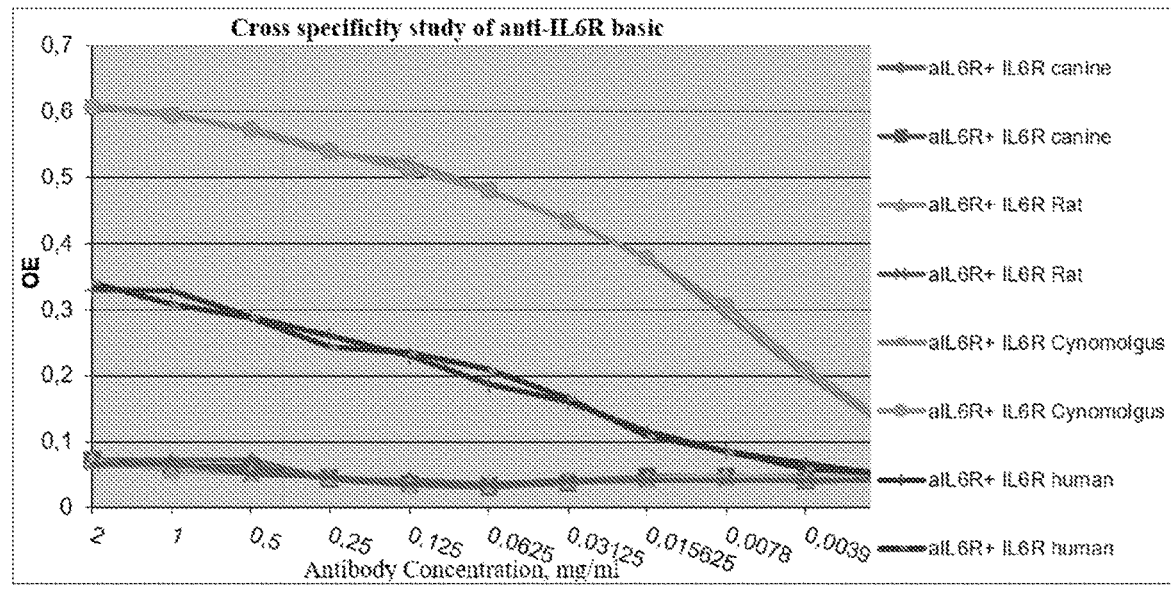

FIG. 11 is enzyme immunoassay of interaction of BCD089 antibody with IL-6R of a human, cynomolgus, rat and dog.

Figure 12:
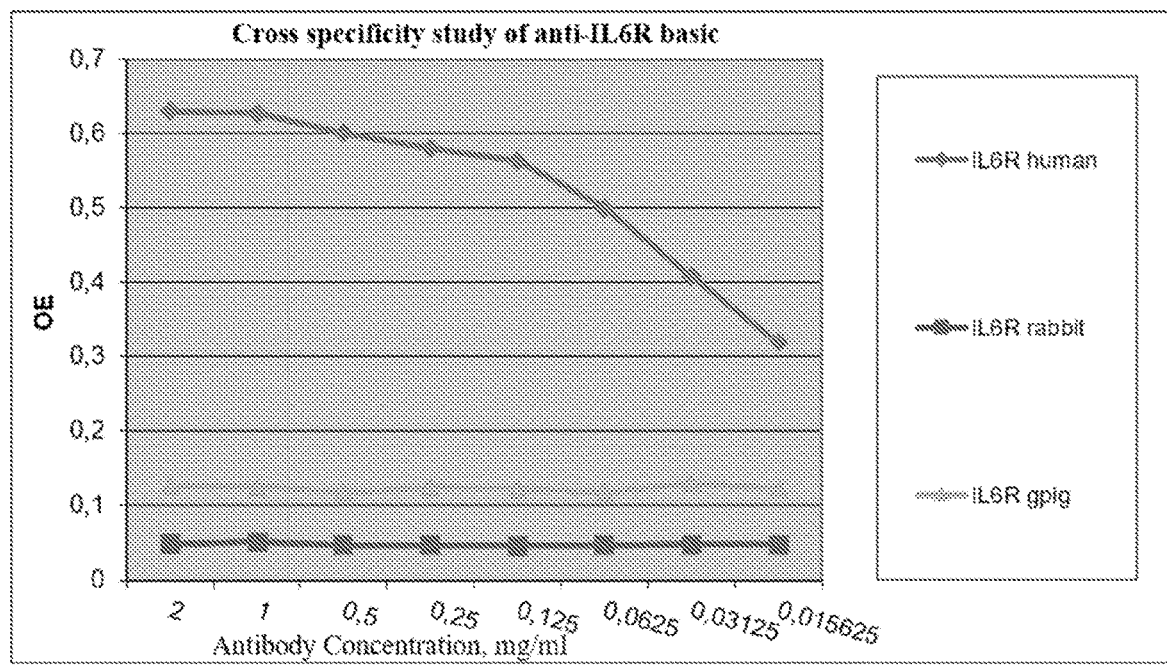

FIG. 12 is enzyme immunoassay of interaction of BCD089 antibody with IL-6R receptors of a human, rabbit and guinea pig.

Figure 13:
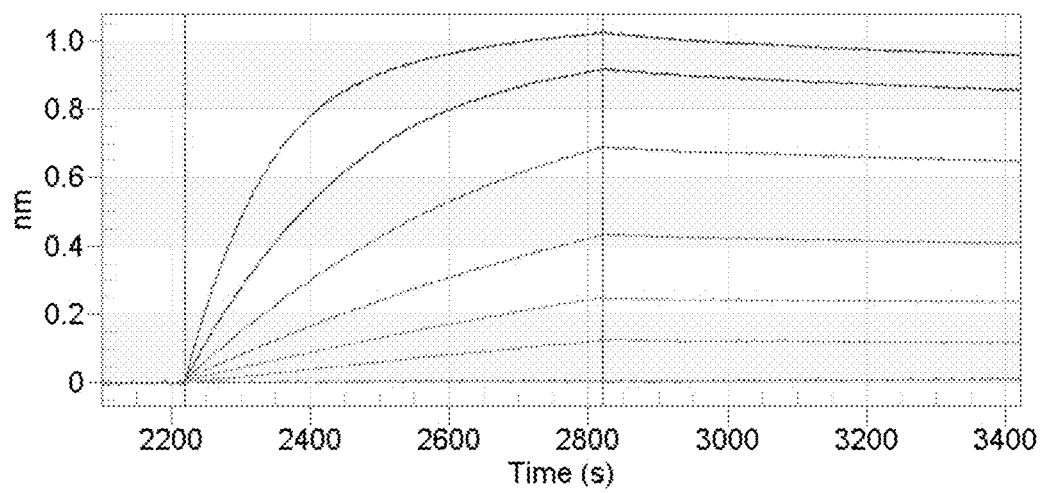

FIG. 13 are association and dissociation kinetics of BCD089 with a human IL-6R alpha subunit using ForteBio.

Figure 14:
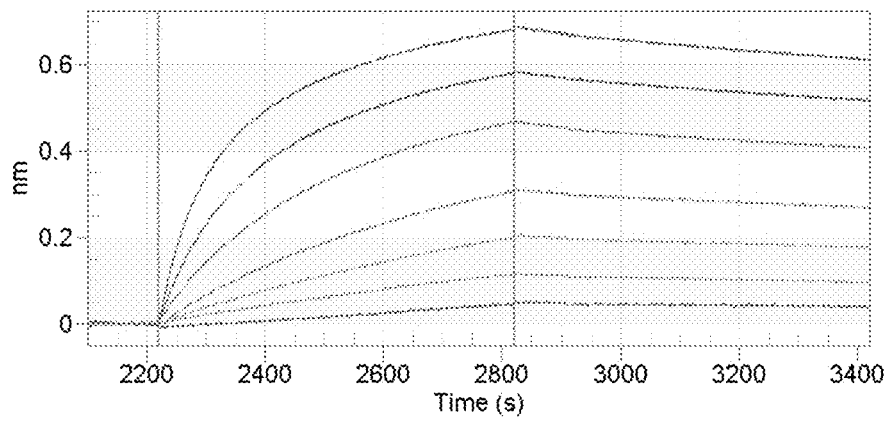

FIG. 14 are association and dissociation kinetics of BCD089 with a cynomolgus IL-6R alpha subunit using ForteBio.

Figure 15:
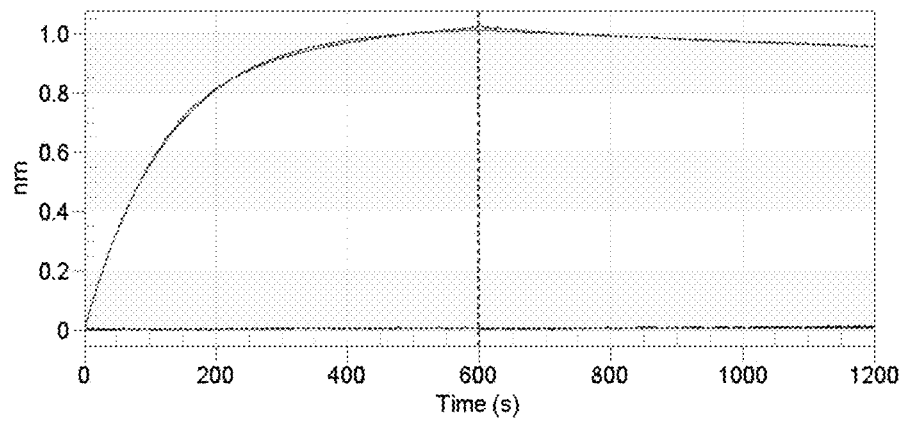

FIG. 15 are association and dissociation kinetics of BCD089 of BCD089 antibody to IL-6R of a human and mouse (a mouse IL-6R of 250 nM—a black curve, a human IL-6R of 50 nM—a blue curve)

Figure 16:
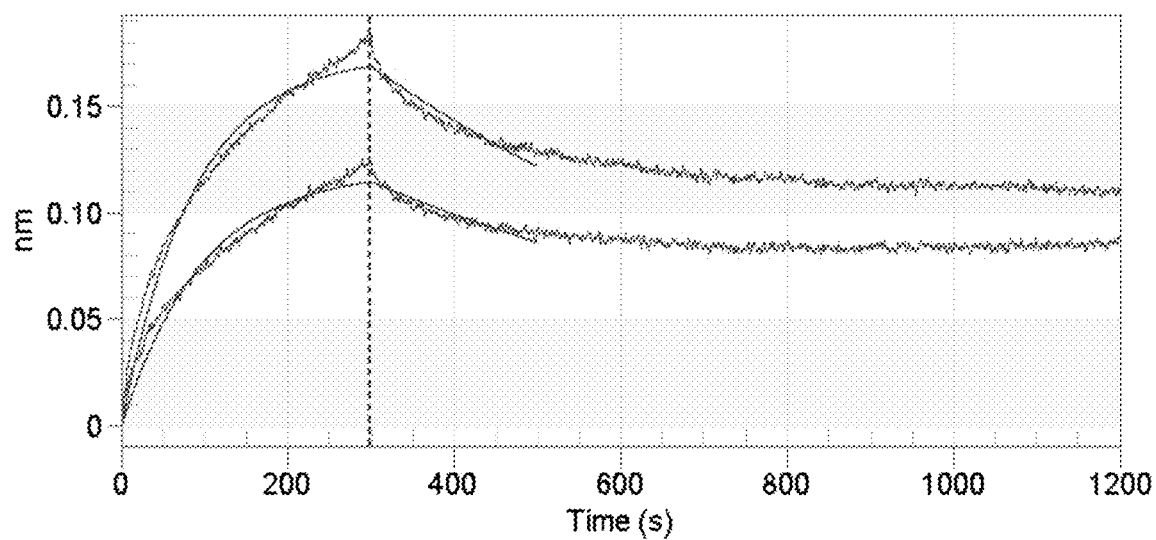

FIG. 16 are association and dissociation kinetics of BCD089 with a guinea pig IL-6R alpha subunit using ForteBio.

Figure 17:
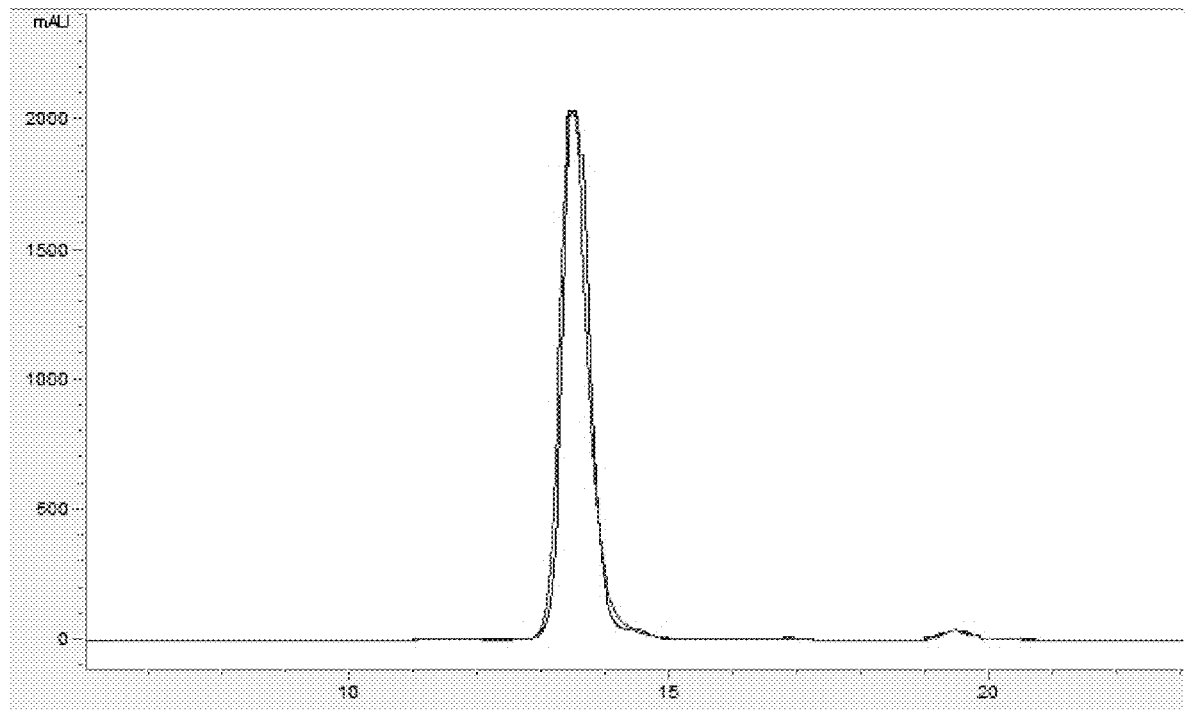

FIG. 17 are gel filtration profiles of BCD089 molecule before (red) and after 12-hour incubation at 50° C. (blue).

Figure 18:
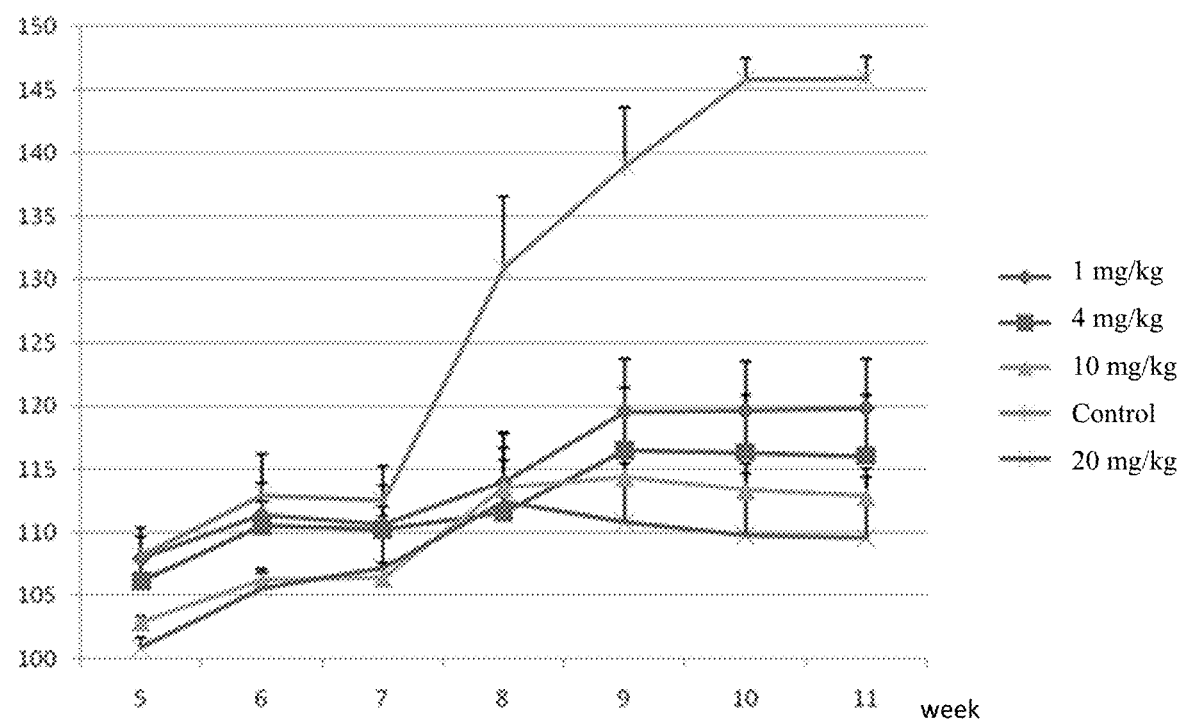

FIG. 18 is assessment of anti-inflammatory activity of BCD-089 product using the primate model of collagen induced arthritis

EMBODIMENT OF THE INVENTION

General Description of a Method for Obtaining and Testing Antibodies of the Invention At the first stage, polypeptides that specifically bind to the soluble form of a human interleukin-6 receptor (sIL-6R), i.e. to α-subunit thereof, were selected. For this purpose, phage libraries designed on the basis of amino acid sequences of heavy and light chains of human immunoglobulins were used. In order to built a phage library RNA molecules were separated and purified from blood of over 1000 donors, of which (molecules) genes of heavy and light chains of donor immunoglobulins were synthesized by reverse transcription and PCR in several stages. Various combinations of genes from binding regions of heavy and light chains were embedded in bacteriophage vectors in a proper orientation and used for creation of hybrid phage libraries (FIG. 4).

The obtained phage libraries were selected on a human sIL-6R protein, which was cultured in a transient CHO-T cell system, and purified from a culture cell fluid on IMAC BIORAD sorbent.

Cells generating sIL-6R were obtained by recloning of alpha subunit gene of a human interleukin-6 receptor into a vector for transient culturing of pEE with subsequent CHO-T transfection.

Producer cell were cultured in an incubator for 7-10 days.

Protein was purified in a single step; target protein was verified by Western blot using specific antibodies (Human IL-6sR Detection antibody Part No. 840244 from Human IL-6sR DuoSet ELISA Development Kit Catalog Number: DY227 R&D System).

The obtained phage libraries were selected in two or more stages. Phages specifically binding to sIL-6R immobilized on plastic were selected. As a result, a plenty of phages binding to sIL-6R from which bacteriophage vectors had been separated were obtained. From these vectors genes of polypeptides specifically binding to a protein were amplified and recloned in expression vectors for synthesis of protein molecules in E. coli prokaryotic cells. After the transformation of cells obtained with plasmids and synthesis of individual polypeptides, we screened and selected molecules specifically binding to IL-6sR and blocking binding of a ligand to a receptor. Affinity constants of the obtained proteins were compared with each other and embedded in the most successful genes of pEE expression vectors for expression of antibodies already full size. After the culturing of antibodies in a suspended cell culture of Chinese hamster ovaries (CHO) and their purification, their affinity was evaluated and various functional cell tests assured that the interleukin-6 signal was blocked. As a result of the performed studies and analysis one molecule of an antibody specifically binding to sIL-6R and blocking the activity of IL-6 in cell tests was selected. Its nucleotide sequences of heavy and light chains were recloned in psX vector with a help of which we obtained cell lines stably producing an antibody. Then, with the obtained cell line the selected antibody, for which the purification scheme and storage conditions had been selected, was cultured. We designed and started pre-clinical studies of the obtained medicinal product.

Example 1

Production of Recombinant Antigens and Antibodies in a Suspended Cell Culture of Mammals Antibodies and antigens were produced in cells of a transient cell line obtained from of Chinese hamster ovary cells (line CHO-K1); according to protocols. The suspension culturing was performed in flasks on an orbital shaker using serum-free media for suspended cultures by Life Technologies Corporation according to manufacturer's instruction. For transient expression cells were transfected with linear polyethyleneimine (PEI "MAX", by "Polysciences"). The DNA/PEI ratio was 1:3-1:10. 7-10 Day after the transfection, the culture medium was centrifuged at 2000 g for 20 minutes and filtered through a 0.22 μm pore size filter. Target proteins were isolated from culture liquid by affine HPLC.

Example 2

Figure 1:
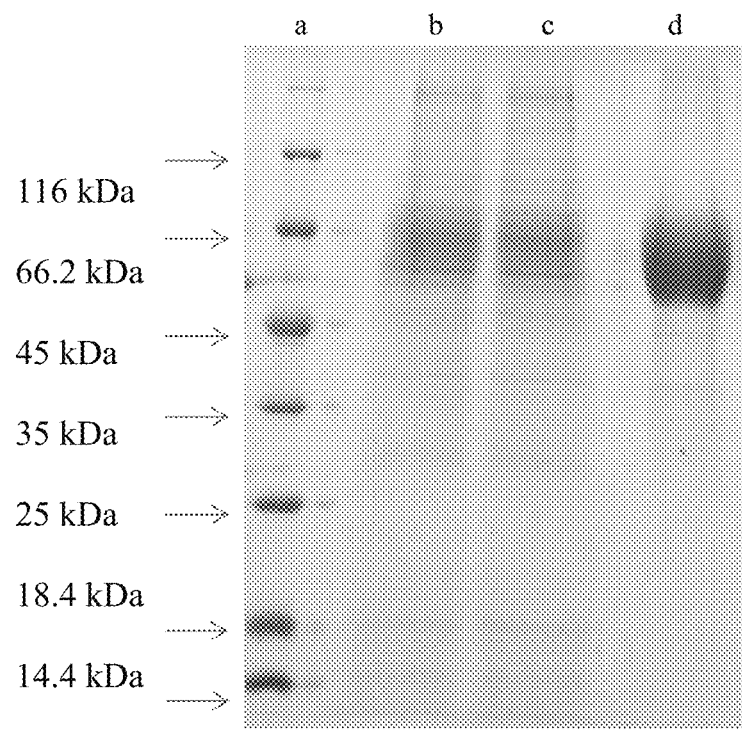
FIG. 1 is a gel electrophoresis under denaturing conditions of the cultured and purified human sIL-6R in a 12% PAGE.

Purification of Antigens and Antibodies from Suspended Cell Culture of Mammals sil-6R Recombinant protein comprising six His amino acids at the protein C-terminus was separated and purified from culture medium using Profinity IMAC Ni-charged resin (by Bio-Rad). Before the purification $NiCl_2$ until its concentration is 1 mM was added in the culture medium. Then 1/200-1/500 of Profinity IMAC Ni-charged sorbent volume was added in the culture medium and mixed in a shaker for 1 hour at room temperature. Then sorbent was transferred onto Thermoscientific Polypropylene columns having a volume of 5 or 10 ml, rinsed with 5 column volumes of 10 mM pH8 phosphate buffer with 5 mM imidasole and 0.3 M sodium chloride to wash non-specifically binding components. The bound antigen was eluted using 0.3 M imidasole, pH 8 0.3 M NaCl. Then the protein was transferred into PBS (pH 7.4) by dialysis using Snake Skin Dialysis Tubing technology, filtered (0.22 μm) and transferred into tubes. The tubes were stored at −70° C. Purity of the obtained solution was assessed with SDS gel electrophoresis, and identified by Western blot techniques using a specific anti-IL-6R antibody and conjugated goat anti-human antibody antibodies (see FIGS. 1 and 2).

The investigated anti-IL-6R antibodies were purified using a 1 ml HiTrap rProteinA FF column (GE Healthcare). Clarified culture liquid was passed through 1 ml HiTrap rProtein A FF (GE Healthcare), which was equilibrated with a phosphate-buffer saline (PBS, pH 7.4). Then the column was washed with 5 column volumes of PBS to remove non-specific bound components. The bound protein was eluted using a 0.1 M glycine buffer pH 3. The major elution protein peak was collected and its pH was neutralized by a 1 M Tris buffer, pH 8. All the stages were performed at flow rate of 1 ml/min. Then the protein was transferred into PBS (pH 7.4) by dialysis using Snake Skin Dialysis Tubing technology, filtered (0.22 μm), transferred into tubes, and stored at −70° C. Purity of the obtained proteins was assessed with SDS gel electrophoresis (see FIGS. 7 and 8).

A recombinant IL6-H6-EPEA ligand (interleukin-6 with a "peptide tail" of 6 histidines and EPEA-tags on C-terminus) were purified on GE Healthcare C16/20 column with a 5 ml Capture Select C-tag Affinity Matrix. All the stages were performed at flow rate of 5 ml/min. Clarified culture medium was processed through the column, which was equilibrated with a phosphate-buffer saline (PBS, pH 7.4). Then the column was washed with PBS until a chromatography system spectrophotometer signal reached a plateau to remove non-specific bound components. A binding protein was eluted using 20 mM Tris 2M MgCl2 pH 7.1. The major eluted protein peak was collected and transferred into PBS (pH 7.4) by dialysis using Snake Skin Dialysis Tubing technology. Then it was filtered (0.22 μm) and transferred into tubes and stored at −70° C. Purity of the obtained solution was assessed with SDS gel electrophoresis (see FIG. 3).

Example 3

Selection of Fab-Libraries of Human Phage Antibodies.

A phage with Fab-fragments specifically binding to sIL-6R were separated from a combinatorial phage Fab-displaying library MeganLib™ (BIOCAD) comprising over $10^{11}$ of individual clones and synthesized on the basis of variable domain of human immunoglobulin genes (FIG. 4) according to a modified protocol (J BiolChem. 1999 Jun. 25; 274(26): 18218-30). In order to generate this library lymphocytes of more than a thousand of donors were used. The selection was performed on recombinant human sIL-6R-H6F under conditions as described above (NatBiotechnol. 1996 March; 14(3):309-14; J Mol Biol. 1991 Dec. 5; 222(3): 581-97). In order to perform selection by panning, sIL-6R-H6 or sIL-6R-Fc of a human was adsorbed in 50 mM of a carbonate buffer (pH 9.5) at 4° C. overnight on the surface of Immune tubes EIA/RIA high binding (Greineer bio-one). The tubes were washed several times with PBST (PBS pH 7.4 and 0.1% Tween 20 v/V), and then vacant protein binding sites on the surface of the tubes were blocked with non-fat milk solution (0.5% m/V in PBST pH 7.4). The non-fat milk solution was incubated in tubes for 1 h. The tubes were then washed with PBST solution. Then, MeganLib™ phage libraries were diluted in 2-4 ml of PBST solution with a 0.5% of non-fat milk until final concentration of phages was $10^{13}$ per ml. The prepared libraries were added into tubes with antigen bound on their surface and incubated for 1 hour while stirring. Unbound phages were removed by series of washing of tubes with PBST. The amount of washing was increased from the first round to the third round: 20-30-40 times, respectively. Phage particles which remained bound were eluted from a plastic tube with 0.1 M Gly-HCl solution (pH 2.2) for 15 min while stirring. Then the solution was transferred into clean plastic tubes and neutralized with 1M Tris-HCl (pH 8) 5:1. *E. coli* TG1 strain bacteria were infected with the obtained phages, the phages were amplificated and used in the next selection cycle.

Example 4

Bacteriophage Amplification

After the selection a bacteriophage was cultured using an *E. coli* TG1 strain. Amplification was carried out by infecting the host strain with phage culture followed by growing for 12-15 hours. After the selection a phage solution was mixed with *E. coli* TG1 grown cell culture ($OD_{600}$=0.3-0.4) and incubated for 1.5 hours at 37° C. Then the cells were spun down at 3000-4000 rpm for 10-15 minutes, resuspended in a 1 ml of 2TY medium and crumbled in Petri dishes with an antibiotic for selection (ampicillin). Colonies were grown in a 30 C thermostat overnight. After 12-15 hours the number of colonies was counted and washed away from the dishes with 5-10 ml of 2TY medium. For this purpose, 100 mcl of cell suspension were added to 20 ml of 2TY medium with an antibiotic (ampicillin) and grown on a shaker till $OD_{600}$ is 0.35-0.5 at 37C. K07 phage helper was added into cell suspension to final concentration $10^{10}$ particles per ml (1 mcl K07 phage helper per 10 ml cell suspension) and incubated at 37C for 1.5 hours while light stirring. Then, an even volume of medium with single-dose of ampicillin (100 µg/ml) and double-dose kanamycin (60 µg/ml) and double-dose IPTG (0.2 mM) were added to the cell culture. Flasks were loaded into a shaker and the phages was cultured for 3-5 hours at 30C. The cell culture was centrifuged for 20-30 min at 10,000 rpm and supernatant was collected in tubes. After this, ⅙ of the solution volume comprising 20% of polyethyleneglycol and 2.5 M of sodium chloride was added into supernatant and stirred intensively. The solution was incubated in ice for at least 3 hours. Then the solution was centrifuged for 10 minutes at 8000 g, the formed sediment comprising phages was diluted in 1 ml of TBS buffer.

Example 5

Recloning Genes of Fab-Fragments with Various Variable Regions in Expression Plasmid.

A phage DNA (phagmid) of a derived M13 phage was separated from *E. coli* TG1 cells after the third selection round. Genes of Fab-fragments with various variable regions were amplificated and recloned into p114 plasmid using the PCR and terminal specific primers. Genes were recloned by sites NheI, NotI. The insertion was checked by sequencing of 4 random colonies.

Example 6

Growing Fab-fragments in *E. coli* BL21Gold Cells with Protein Expression into Growth Cell Medium.

Fab-fragments based on the obtained genes were synthesized in *E. coli* BL21Gold cells. pLL4 Expression vector with genes of Fab-fragments recloned into it from phagmides after selection round 2 and 3, were transformed (electroporated according to the standard protocol) into an expression strain of *E. coli* BL21Gold. Cells were grown in 2TY culture medium onto agarized medium (Petri dishes) with selective antibiotics (kanamycin 30 µg/ml, ampicillin 100 µg/ml and glucose 0.2%). Cells were grown in a such a manner that cell titer is suitable of selecting individual clones; colonies were grown for 14-16 hours in a thermostat at 30C. Certain colonies were reinjected into 96 well plates (U-shape) with 100 mcl of 2TY medium (kanamycin 30 µg/ml, ampicillin 100 µg/ml and glucose 0.4%) per well and grown on a shaker at 800 rpm for 16-18 hours at room temperature. Cell cultures were screened out through a 96-channel replicator onto sterile 96 well plates (V-shape) with 100 mcl of 2TY medium (kanamycin 30 µg/ml, ampicillin 100 µg/ml and glucose 0.1%, TX100 0.01% and IPTG 0.5 mM) and grown on a shaker at 800 rpm at room temperature overnight. The plates were centrifuged at 3500 rpm for 20 min and a medium with Fab-fragments for ELISA were collected in clean 96 well plates (U-shape), the plates were stored at −70C.

Example 7

Screening of Fab of Specific Binding with Human IL-6sR-H6

ELISA was used to select Fab fragments that specifically bind to human IL-6sR-H6. Fab Actemra (tocilizumab) reproduced [US20110245473 seq.id 15 and US20110245473 seq.id 16] was used as a positive control. For screening of specific binding, 96 well ELISA plates were used (by NuncImmunoMaxisorp). IL-6sR-H6 antigen binding was carried out on the well surface; to this end, 50 µl of IL-6sR-H6 solution (0.5 µg/ml) in binding carbonate buffer was added to each well. Plates was covered and incubated overnight at 4° C. All subsequent steps were performed following standard ELISA protocol using a high-throughput automated platform based on robotic systems Genetix Qpix2xt (Molecular Device) and Tecan Freedom EVO 200 (Tecan). The following day the plate wells were washed 5 times with PBST. A blocking buffer 200 µl per well of 0.5% non-fat milk in PBST was added to the plates to prevent non-specific binding. Plates were incubated on a shaker for 1 h at room temperature. After washing with PBST, 50 µl of 1:1 mixture of the test cell supernatant, containing the test Fabs, and blocking buffer was added to each well. Plates containing Fab solutions were incubated on a shaker for 1 h at room temperature. After 1 hour, the plate wells were washed 5 times with PBST. Then a solution of conjugated goat secondary antibody anti-human Fab with peroxidase (by Pierce ThermoScientific) (1:5000) in PBST was added to the plate wells (50 mcl per well). Plates were shaken in a rotation shaker (50 min at room temperature) and then 5 times washed with PBST as described above. A colorimetric signal was obtained by adding TMB substrate solution in acetate buffer pH5.5 and $H_2O_2$ 0.02% (50 mcl/well), was incubated until obtaining a saturated signal (3-5 min on average), the reaction was stopped by adding a 10% sulphuric acid solution (30 µl/well). The signal was measured at 450 nm with Tecan-Sunrise plate reader (Tecan). The number of Fabs bound to antigen was proportionate to the signals registered. Therefore, clones were selected, the signal of which exceeded the background signal by more than 5 times. The selected Fabs were then checked in a competitive ELISA to detect antagonistic Fabs blocking interaction between IL6 and its receptor. *E. coli* BL21Gold cell suspensions with maximum signals were transferred to clean plates and incubated in 15% glycerol at −70C.

Example 8

Competitive ELISA Blocking Interaction of IL6 Ligand and IL-6R Receptor with Fab-Fragments A competitive ELISA was used to check antagonistic ability of previously selected Fab-fragments to specifically bind to a human IL-6R. As a positive control of an antagonist we used anti-IL-6R Fab fragment. A ligand IL-6-EPEA was immobilized on ELISA plates (Maxisorp) by adding to a well 50 mcl of a protein solution (1 µg/ml) in a carbonate buffer. The solution was incubated in a plate at 4° C. overnight. All the subsequent stages were performed following a standard ELISA technique, with some changes, using a high-performance automated platform based on GenetixQ-pix2xt robotic system (by MolecularDevice) and TecanFreedom EVO 200 (by Tecan). In order to block nonspecific binding a blocking buffer (200 mcl per well, 0.5% of non-fat milk in PBST) was added. Plates were incubated on a shaker for 1 h at room temperature.

In parallel with that each 50 mcl of the tested cell supernatant comprising investigate Fab-fragments of anti-IL-6R were mixed with 50 mcl of IL-6sR-H6F receptor solution (0.4 µg/ml in 1% non-fat milk in PBST) in a non-binding 96 well plate. It was incubated for 1 hour at 37° C. on a shaker at 500 rpm.

After a blocking buffer was washed away from the plates with immobilized ligand IL6, the abovementioned reaction mixture of Fab-fragments of anti-IL-6R and IL-6sR receptor was transferred in those plates. The plates were again incubated on a shaker for 45 minutes at room temperature, and then the plates were washed five times with PBST buffer. A mouse antibody of anti-FLAG (FLAG peptide is a C-terminus peptide on IL-6sR-H6F protein) in PBST was added (50 µl/well) and incubated for 45 minutes under the same conditions. The plates were five time washed with PBST buffer, then goat anti-mouse peroxidase conjugated antibody products by Pierce in PBST were added (dilution of 1:5000). As before the plates were incubated on a shaker for 45 minutes at room temperature, and then were washed five times with PBST buffer. A colorimetric signal was obtained with TMB solution (50 mcl/well) until saturated (3-5 min on average), the reaction was stopped by adding a 10% sulphuric acid solution (30 mcl/well). A colour signal was measured at a 450 nm wave length using Tecan-Sunrise plate reader (by Tecan). The degree of secondary conjugated antibody binding was proportionate to the colour signal.

Clones which indicated signal blocking at the level of a controlled Fab-fragment of anti-IL-6R were selected and used during further analyses. Genes of variable domains of selected, after this stage, clones were sequenced according to standard protocols on AppliedBiosystems 3130GeneticAnalyzer (AppliedBiosystems) and analyzed.

Example 9

Comparative koff (kdis) Screening of Anti-IL-6R Fabs

Fab-fragments specifically binding to IL-6R receptor, and blocking interaction of the receptor with its ligand were compared with each other by the affinity for a receptor. Comparative koff (kdis) screening of anti-IL-6R candidates was performed using Octet Red 96 and anti-FABCH1 biosensors (Pall-ForteBio) (FIG. 6). The biosensors were rehydrated in a running buffer comprising 10 mM PBS pH 7.2-7.4, 0.1% Tween-20 and a 0.1% BSA. 1/10 of the volume of 10× running buffer was added in the investigated samples of the E. Coli cell growing medium comprising anti-IL-6R Fab-fragments and mixed. Then anti FABCH1 biosensors were immersed in solutions comprising Fab-fragments for 12 hours at 4° C. After 12 hours the sensors with surface-immobilized Fab-fragments transferred into wells with running buffer, where a baseline (60 sec) was set. The sensors were then transferred to wells with an analyte solution (IL-6sR-H6F, 30 µg/ml) to achieve antigen/Fab-fragment complex association (300 sec). After that, sensors were returned into wells with working buffer for further dissociation (300 sec). Used sensors were subject to regeneration after each test: they were three times placed into regenerating buffer (Gly-HCl, pH 1.7) and then used in further experiments. The curves obtained were analyzed using OctetDataAnalysis (version 7.0) according to the standard procedure with 1:1 interaction model.

The results of koff screening of anti-IL-6R candidates are shown in Table 1. Specific binding of all Fab-fragments with a human IL-6R was demonstrated, candidates with minimum value were recloned to obtain full-length antibodies.

TABLE 1

Check of kdis of Anti-IL-6R Fab-fragments with Alpha Subunit of Human Interleukin-6 on ForteBio

| No. | Clone name | K off ForteBio |
|---|---|---|
|  | Control Fab-fragment | 7.91E−04 |
| 1 | >Il6R__CVKSel2__MMP1A4__14 | 7.63E−04 |
| 2 | >Il6R__CVKSel2__MMP1A6__16 | 7.84E−04 |
| 3 | >Il6R__CVKSel2__MMP1C12__165 | 1.27E−04 |
| 4 | >Il6R__CVLSel2__MMP1G11__52 | 2.64E−04 |
| 5 | >Il6R__CVLSel2__MMP1H6__113 | 6.37E−04 |
| 6 | >Il6R__CVLSel2__MMP1H9__118 | 6.28E−04 |
| 7 | >Il6R__CVLSel2__MMP1H10__119 | 6.50E−04 |
| 8 | >Il6R__CVLSel2__MMP2A2__129 | 6.41E−04 |
| 9 | >Il6R__CVLSel2__MMP2A4__133 | 1.05E−03 |
| 10 | >Il6R__CVLSel2__MMP2A5__134 | 7.00E−04 |
| 11 | >Il6R__CVLSel2__MMP2A8__143 | 6.89E−04 |
| 12 | >Il6R__CVLSel2__MMP2B2__176 | 3.14E−04 |
| 13 | >Il6R__CVLSel2__MMP2B3__177 | 5.81E−04 |
| 14 | >Il6R__LVLSel2__MMP2C10__367 | 4.79E−04 |

Example 10

Construction of Full-Length IgG1 Antibodies by Recloning Variable Domains from Fab-Fragments.

Full-length IgG1 antibodies were constructed by recloning of variable domain genes from expression plasmids used previously for culturing Fab-fragments. In-Fusion® HD EcoDry™ CloningKit by Clontech was used for the recloning. Variable domain genes insertions were obtained by PCR with specific primers, matrix plasmids in the PRC were removed by treatment with the DpnI restrictase. The pEE plasmid vector was linearized by restriction of SalI and BsiWI restrictases for a light chain and SalI/NheI for a heavy one. The gene insertion and linearized vector were mixed in 10 mcl of water and transferred into separate strip vials of the In-Fusion system. Stir by pipetting. The strips were incubated for 15 minutes at 37° C., then for 15 minutes at 50° C., then they were transferred into ice. Part of the reaction volume with the obtained construction was used for the cell transformation. Plasmids were extracted from the obtained clones and the insertion was checked by sequence.

Example 11

Cell Inhibition Test for DS-1 Cell Proliferation with Anti-IL-6R Antibodies.

The DS-1 cell growth depends on the presence of an extracellular external IL6 ligand and blocking of its binding to a receptor on the cell surface results in their cell growth inhibition. The DS-1 cell culture was grown on RPMI-1640 medium supplemented with 10% inactivate fetal bovine serum, 1 mM of sodium pyruvate and 7.5 ng/ml of IL6. A day before the experiment cells were washed two times in PBS from IL6 residues and plated into a 96 well plate at the rate of 1000 cells/well in a growth medium without adding IL6. The following day a range of antibody diluted solutions from 20 µg/ml with spacing 3 in the full growth medium with addition of 5 ng/ml of IL6 was prepared. Then, the cells were added an even volume of prepared antibody solutions, the final concentration of IL6 in wells was 2.5 ng/ml, of antibodies in the first point—10 µg/ml. The cells were incubated at 37° C., 5% $CO_2$ for 3 days. Then, a number of living proliferating cells was measured with AlamarBlue vital dye on FluoroskanAscent FL 2.5 (FIG. 9). Following the results of the study one anti-IL-6R antibody which maximally inhibits DS-1 cell proliferation was selected, therefore, it binds to a membrane receptor of interleukin-6 and blocks the binding of a ligand with a receptor.

Example 12

STAT3 Inhibition Analysis in HEK-Blue™ IL6 Cell Culture

HEK-Blue IL6 cell suspension was prepared with concentration of $1*10^6$ clones/ml in DMEM medium supplemented with 10% of inactivated fetal bovine serum (cell growth medium). The cells were plated into a 96 well plate at the rate of 100 mcl/well ($5*10^4$ clones/well).

A range of antibody diluted solutions was prepared in the cell growth medium from 200 µg/ml with spacing 3 ten points, the last point was control, without antibody. A human IL6 solution was prepared in the cell growth medium with concentration of 4 ng/ml. Then, the cells were added by 50 mcl of diluted antibodies and incubated for 45 minutes in a $CO_2$ incubator. The cells with antibodies were added by 50 mcl of IL6 solution and the cells were left for incubation with antibodies and IL6 overnight in a $CO_2$ incubator.

The following day QUANTI-Blue™ detection medium was prepared: 1 pack of a dried medium was dissolved in 50 ml of purified water, heated on a waterbath at 37° C. for 10 minutes and filtered through a 0.22 µm filter.

Each well with 180 mcl of detection medium was added 20 mcl of culture cell fluid and was left in a $CO_2$ incubator for 2-3 hours. The absorbance level was measured on a spectrophotometer at a wave length of 630 nm (FIG. 10).

Example 13

Determination of Binding Affinity Constant of BCD89 Antibody to Human Interleukin-6 Receptors and its Orthologues.

The interaction of the selected anti-IL6R with interleukin-6 receptors of cynomolgus, guinea pig, dog and mouse was examined with ELISA (FIG. 11, 12). The binding affinity constants of BCD89 antibody to IL-6sR alpha subunit of a human, cynomolgus, guinea pig, dog and mouse were obtained with Octet Red 96 (by ForteBio). BCD89 was nonspecifically immobilized onto the surface of amino reactive sensors of the second generation (AR2G) using standard protocol according to manufacturer's instruction for preparation and immobilization of AR2G sensors. Analysis was conducted at 30° C. using PBS comprising 0.1% Tween-20 and 0.1% BSA as a working buffer. Titration of IL-6R of a human, cynomolgus, guinea pig, dog, rabbit and mouse was performed using a running buffer from concentration of 126 nM to 2 nM, spacing 2.

Binding curves, after subtracting a reference signal, were analyzed using Octet Data Analysis software (Version 7.0) in accordance with the standard procedure and using 1:1 interaction model. The results are shown in Table 2.

As can be seen, BCD89 binds to a recombinant IL-6R of a human and IL-6sR of a cynomolgus with a high affinity (see FIG. 13, FIG. 14). Moreover, a candidate interacts with a guinea pig IL-6R with the constant being lower by 3 orders than with a human one (see FIG. 16). Interaction with a mouse receptor was not registered (see FIG. 15).

TABLE 2

Analysis of Interaction of BCD89 Candidates with IL-6sR Receptors of human and different organisms using Octet RED

| | Human sIL6R KD, M | Cynomolgus sIL6R KD, M | Guinea Pig sIL6R KD, M | Mouse sIL6R KD, M |
|---|---|---|---|---|
| BCD-BCD-089 IgG1 | 6.63E−10 | 2.40E−09 | 3.06E−07 | — |

Example 14

Determination of BCD89 Aggregative Stability under Thermostress Conditions.

Investigated samples were concentrated until 5 mg/ml by ultrafiltration in centrifuge filters AmiconUltra of 10 kDa/0.5 ml (Millipore). The protein content was determined by UV spectrophotometry at a wave length of 280 nm. Each obtained sample was divided into several parts by 150 mcl and transferred into separate tubes: one tube of each compound was put into a refrigerator for storage at +4° C., the other tubes were placed in a thermostat for tubes and thermostated at 50° C. for the set time.

Once heated, the tubes were removed from the thermostat, cooled till room temperature, clarified by centrifuging solutions at 13,000 g for 10 minutes, supernatants were delivered for gel filtration with UV detector. Full size protein peaks on chromatograms were analyzed before and after the heating, chromatography was performed on Agilent USA 1100 series M chromatograph. A column Tosoh TSK-Gel G3000SWXL 7.8 mm ID×30 cm and pre-column Tosoh TSK-Gel Guard-SWXL 6 mm ID×4 cm, 7 mcm were used. Flow rate was 0.7 ml/min, the sample volume—10 mcl with the sample concentration of 5 mg/ml. Detector wave length–220 and 280 nm, elution time–25 min (FIG. 17).

Calculations were performed by the internal normalization method. A percentage content of monomer (X) was calculated by formula:

$$X = \frac{S_1 \cdot 100}{\Sigma S},$$

where S1—the monomer peak area;
ΣS—the sum of all peak areas.

During the calculations, peaks which are present on moving phase chromatograms and the prescribed buffer solution were disregarded.

Example 15

Assessment of Anti-inflammatory Activity of BCD-089 Product using the Primate Model of Collagen Induced Arthritis.

The study was performed in males of cynomolgus monkeys (*Macaca fascicularis*) using the primate model of collagen induced arthritis. A total number of animals involved in the experiment amounted to 20 heads, each group included 4 monkeys. Four dosing levels of the product were used during the experiment: 1.0 mg/kg; 4.0 mg/kg; 10.0 mg/kg; 20.0 mg/kg, animals of control group were administered with placebo. Administration of the product and placebo started after preliminary sensitization with collagen. During the experiment, the animals of all groups were measured to calculate the articular surface and percentage of inflammation area (PIA), at the end of the research metacarpophalangeal and metatarsophalangeal joints were taken to assess the severity of destructive changes. Animals were distributed into 5 groups. Names of the groups are shown in Table 3.

TABLE 3

Groups of Animals in the Study of Anti-inflammatory Activity

| Group no. | Animal qty | Substance | Route of administration | Dose |
|---|---|---|---|---|
| 1 | 4(♂) | MAb against IL-6R | s/c | 1.0 mg/kg |
| 2 | 4 (♂) | | | 4.0 mg/kg |
| 3 | 4 (♂) | | | 10.0 mg/kg |
| 4 | 4 (♂) | | | 20.0 mg/kg |
| 5 | 4 (♂) | Placebo | | — |

For arthritis induction, the emulsion of bovine type II collagen (Sigma) was three times administered to animals.

The first administration of collagen. Total amount of administered collagen was 2 mg per one experimental animal. For this purpose, 2 mg of collagen were dissolved in 0.7 ml of 0.1 M acetic acid. 0.7 ml of Freund's incomplete adjuvant was added to this solution.

Animals were kept for 28 days after the first administration of collagen.

The second administration of collagen. Total amount of administered collagen was 3 mg per one experimental animal. For this purpose, 3 mg of collagen were dissolved in 1.0 ml of 0.1 M acetic acid. 1.0 ml of Freund's complete adjuvant was added to this solution.

Animals were kept for 21 days after the second administration of collagen.

The third administration of collagen. Total amount of administered collagen was 3 mg per one experimental animal. For this purpose, 3 mg of collagen were dissolved in 1.0 ml of 0.1 M acetic acid. 1.0 ml of Freund's incomplete adjuvant was added to this solution.

Measuring the size of the joints was carried with calipers in the following time points:
before the first administration of collagen
at the time of the second administration of collagen
weekly after the second administration immediately before the administration of collagen for 7 weeks.

During the measurement process the amount of longitudinal and transverse axis of the joint was estimated; this procedure was carried out for all the metacarpophalangeal and metatarsophalangeal joints except the thumb. Calculation of the area was carried out by the formula:

JA=the value for the longitudinal axis×the value for the transverse axis×3.14×0.25.

The data for 16 joints of each animal were used to calculate the values of percent of inflammation area (PIA). Calculation was carried out by the formula:

PIA=(the JA value on the day of the experiment×100)/(the average value for the JA before the induction of arthritis) (FIG. 18).

Example 16

Study of Toxicity and Pharmacokinetics (Toxicokinetics) of BCD-089 Product Following a Single Subcutaneous Administration in Rhesus Monkeys.

The study was performed in 12 males of rhesus monkeys. Animals were divided into 4 groups. Names of the groups are shown in Table 4.

TABLE 4

Groups of Animals in the Study of Toxicokinetics

| Group no. | Animal qty | Substance | Route of administration | Dose |
|---|---|---|---|---|
| 1 | 3 (♂) | MAb against IL-6R | s/c | 2.0 mg/kg |
| 2 | 3 (♂) | MAb against IL-6R | | 10.0 mg/kg |
| 3 | 3 (♂) | MAb against IL-6R | | 50.0 mg/kg |
| 4 | 3 (♂) | Placebo | | — |

The following parameters were assessed during the experiment:
results of clinical examinations;
animal weight (before administration and on day 8, 15, 22, 29, 36, 43 of the experiment);
body temperature (before administration and after 1, 2, 4, 6, 24 hours after administration, on day 8, 15, 22, 29, 36, 43 of the experiment);
urinalysis (before administration and on day 8, 15, 22, 29, 36, 43 of the experiment);
complete blood analysis on the following parameters: number of erythrocytes, number of leucocytes, hemoglobin concentration (before administration and on day 8, 15, 22, 29, 36, 43 of the experiment);
biochemical analysis of serum on the following parameters: lactate dehydrogenase, total bilirubin, total protein, glucose, aspartate aminotransferase, alanine aminotransferase (before administration and on day 8, 15, 22, 29, 36, 43 of the experiment);
examination of concentration of preparation in the blood serum of primates ((before administration, after 0.5, 1, 3, 6, 24, 30, 48, 72, 96, 120, 192, 264, 408, 504, 720, 912 and 1032 hours after administration).

Example 17

Study of Toxicity Following Multiple Subcutaneous Administration in Cynomolgus Monkeys for one Month Followed by a Period Free from Administrations for Two Weeks.

A study of toxicity following multiple subcutaneous administration for one month followed by a recovery period for two weeks was performed in the relevant animal species-cynomolgus monkeys. Three dose levels were used in the experiment. The scheme of the experimental groups is shown in Table 5.

TABLE 5

Groups of Animals in the Study of Toxicity Following Multiple Administration

| Group no. | Animal qty | Substance | Route of administration | Dose |
|---|---|---|---|---|
| 1 | 3 (♂) 3 (♀) | MAb against IL-6R | s/c | 4.0 mg/kg |
| 2 | 3 (♂) 3 (♀) | MAb against IL-6R | | 15.0 mg/kg |
| 3 | 3 (♂)* 3 (♀)* 3 (♂) 3 (♀) | MAb against IL-6R | | 40.0 mg/kg |
| 4 | 3 (♂) 3 (♀) | Placebo | | — |

The following parameters were assessed during the experiment:
results of clinical examinations;
animal weight (before administration and further every week)
body temperature (before administration and then weekly until termination of the experiment);
effect on cardiovascular system based on bioelectric activity of heart evaluated by Poly-Spectrum cardiograph; evaluation was performed before administration and then on week 3, 5, 7 of the experiment;
urinalysis (before administration and on week 3, 5, 7 of the experiment);
complete blood analysis on the following parameters: number of erythrocytes, number of leukocytes, hemoglobin concentration, number of lymphocytes, number of monocytes, number of neutrophils, number of eosinophils, number of basophils, number of platelets (before administration, and then once a week starting from the first week of the experiment);
evaluation of effect on blood coagulation system on the following parameters:
activated partial thromboplastin time, fibrinogen concentration, prothrombin time—was performed before the product administration, then on weeks 3, 5, 7 of the experiment;
biochemical analysis of serum on the following parameters: sodium, potassium, creatinine, urea, alkaline phosphatase, lactate dehydrogenase, total bilirubin, total protein, glucose, triglycerides, aspartate aminotransferase, alanine aminotransferase, total cholesterol (before administration and on week 3, 5, 7 of the experiment);
at the end of the period of administration, animals of satellite group of maximum dose were euthanized, followed by pathomorphological examination thereof; at the end of the study of the animals from group of maximum dose and control group;
as part of the toxicity study, local irritant effects of products were also evaluated, and soft tissues located near the injection areas were therefore selected and histologically examined.

Example 18

Studies of the Immunogenicity Following Multiple Subcutaneous Administration of BCD-089 Product within 4 Weeks in Cynomolgus Monkeys Examination of immunogenicity in case of multiple subcutaneous administrations for 1 month followed by a recovery period for 2 weeks was performed on a relevant animal—cynomolgus monkeys. Three dose levels were used in the experiment. The scheme of the experimental groups is shown in the Table below.

TABLE 6

Groups of Animals in the Immunogenicity Study

| Group no. | Animal qty | Substance | Route of administration | Dose |
|---|---|---|---|---|
| 1 | 3 (♂) 3 (♀) | MAb against IL-6R | s/c | 4.0 mg/kg |
| 2 | 3 (♂) 3 (♀) | MAb against IL-6R | | 15.0 mg/kg |
| 3 | 3 (♂) 3 (♀) | MAb against IL-6R | | 40.0 mg/kg |

The assessment of immunogenicity was performed on the basis of the binding antibody level, for which purpose blood samples were collected with the following serum separation before the product administration and on weeks 3, 5, 7 of the experiment.

Example 19

Studies of the Pharmacokinetics Following Multiple Subcutaneous Administration of BCD-089 Product in Cynomolgus Monkeys within One Month.

A study of pharmacokinetics following multiple subcutaneous administration for one month followed by a recovery period for two weeks was performed in the relevant animal species—cynomolgus monkeys. Three dose levels were used in the experiment. The scheme of the experimental groups is shown in Table 7.

TABLE 7

Groups of Animals in the Study of Pharmacokinetics Following Multiple Administration

| Group no. | Animal qty | Substance | Route of administration | Dose |
|---|---|---|---|---|
| 1 | 3 (♂) 3 (♀) | MAb against IL-6R | s/c | 4.0 mg/kg |
| 2 | 3 (♂) 3 (♀) | MAb against IL-6R | | 15.0 mg/kg |
| 3 | 3 (♂) 3 (♀) | MAb against IL-6R | | 40.0 mg/kg |

To assess the product level change in blood serum of primates blood samples were collected before the beginning of the experiment and on days 1, 2, 8, 9, 15, 16, 22, 23, 29, 36, and 43 of the experiment.

Example 20

A study of BCD-089 Product Immunotoxicity Following Multiple Subcutaneous Administration for One Month Followed by a Recovery Period for Two Weeks.

A study of immunotoxicity following multiple subcutaneous administration for one month followed by a recovery period for two weeks was performed in the relevant animal species—cynomolgus monkeys. Three dose levels were used in the experiment. The scheme of the experimental groups is shown in Table 8.

TABLE 8

Groups of Animals in the Study of Immunotoxicity

| Group no. | Animal qty | Substance | Route of administration | Dose |
|---|---|---|---|---|
| 1 | 3 (♂) 3 (♀) | MAb against IL-6R | s/c | 4.0 mg/kg |
| 2 | 3 (♂) 3 (♀) | MAb against IL-6R | | 15.0 mg/kg |
| 3 | 3 (♂) 3 (♀) | MAb against IL-6R | | 40.0 mg/kg |
| 4 | 3 (♂) 3 (♀) | Placebo | | — |

The following parameters were assessed during the experiment:
- subpopulation composition of lymphocytes which was evaluated before preparation administration and then on week 2, 4, 6 of the experiment;
- ratio of immunoglobulin classes was evaluated before administration and on week 2, 4, 6 of the experiment;
- effect on phagocytosis was evaluated before administration and on week 2, 4, 6 of the experiment.

Example 21

Obtaining a Pharmaceutical Composition.

BCD089 antibody was transferred into an appropriate buffer till the concentration achieved 180 mg/ml, the obtained solution was filtered (sterilizing filtration) and drawn into syringes.

The invention claimed is:

1. An antibody or antigen-binding fragment thereof having the ability to bind to a human interleukin-6 receptor (IL-6) comprising:

a binding domain comprises a heavy chain that comprises CDR1 comprising the amino acid sequence of SEQ ID NO:1, CDR2 comprising the amino acid sequence of SEQ ID NO:2, and CDR3 comprising the amino acid sequence of SEQ ID NO: 3, and a light chain that comprises CDR1 comprising the amino acid sequence of SEQ ID NO:4, CDR2 comprising the amino acid sequence of SEQ ID NO:5, and CDR3 comprising the amino acid sequence of SEQ ID NO: 6.

2. The antibody or fragment thereof according to claim 1, comprising a heavy chain with an amino acid sequence that is at least 95% identical to the sequence of SEQ ID NO: 9.

3. The antibody or fragment thereof according to claim 1, comprising a light chain sequence that is at least 95% identical to the sequence of SEQ ID NO: 10.

4. The antibody or fragment thereof according to claim 1 that is one of the following human isotypes: IgG1, IgG2, IgG3 and IgG4.

5. The antibody or fragment thereof according to claim 1, wherein the antibody or fragment thereof is of an IgG1 isotype with an Fc constant region, comprising E233P, L234A, L235A, E236P, L237V and/or L238A mutations.

6. The antibody or fragment thereof according to claim 1, wherein the antibody or fragment thereof is of an IgG1 isotype with an Fc constant region comprising M255Y, S257T and/or T259E mutations that increase the value of animal or human pharmacokinetic parameters.

7. A pharmaceutical composition comprising an effective amount of an antibody or antigen-binding fragment thereof according to claim 1, in combination with one or more pharmaceutically acceptable excipients, diluents or carriers.

8. The pharmaceutical composition according to claim 7 wherein it is a solution for parenteral administration.

9. The pharmaceutical composition according to claim 7 in a form of lyophilized powder.

10. The antibody or fragment thereof according to claim 1, comprising a heavy chain with an amino acid sequence that is SEQ ID NO: 9.

11. The antibody or fragment thereof according to claim 1, comprising a light chain with an amino acid sequence that is SEQ ID NO: 10.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Homo sapiens
<220> FEATURE:
<223> OTHER INFORMATION: synthetic

<400> SEQUENCE: 1

Ser Tyr Tyr Met Ser
1               5

<210> SEQ ID NO 2
<211> LENGTH: 16
<212> TYPE: PRT
<213> ORGANISM: Homo sapiens
<220> FEATURE:
<223> OTHER INFORMATION: synthetic

<400> SEQUENCE: 2

Gly Ile Tyr Ser Asp Gly Thr Thr His Tyr Gly Asp Ser Val Lys Gly
1               5                   10                  15

<210> SEQ ID NO 3
<211> LENGTH: 12
<212> TYPE: PRT
<213> ORGANISM: Homo sapiens
<220> FEATURE:
<223> OTHER INFORMATION: synthetic

<400> SEQUENCE: 3

Gly Ala Gly Pro Thr Trp Trp Tyr Ala Leu Asp Ala
1               5                   10

<210> SEQ ID NO 4
<211> LENGTH: 15
<212> TYPE: PRT
<213> ORGANISM: Homo sapiens
<220> FEATURE:
<223> OTHER INFORMATION: synthetic

<400> SEQUENCE: 4

Lys Ser Ser Gln Ser Val Leu Ser Ala Ser Asn Thr Tyr Leu Asn
1               5                   10                  15

<210> SEQ ID NO 5
<211> LENGTH: 7
<212> TYPE: PRT
<213> ORGANISM: Homo sapiens
<220> FEATURE:
<223> OTHER INFORMATION: synthetic

<400> SEQUENCE: 5

Tyr Ala Ser Thr Arg Glu Ser
1               5
```

<210> SEQ ID NO 6
<211> LENGTH: 9
<212> TYPE: PRT
<213> ORGANISM: Homo sapiens
<220> FEATURE:
<223> OTHER INFORMATION: synthetic

<400> SEQUENCE: 6

Gln Gln Ala Tyr Arg Ala Pro Val Thr
1               5

<210> SEQ ID NO 7
<211> LENGTH: 120
<212> TYPE: PRT
<213> ORGANISM: Homo sapiens
<220> FEATURE:
<223> OTHER INFORMATION: synthetic

<400> SEQUENCE: 7

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Thr Thr His Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Leu Asn Ser Leu Arg Ala Glu Asp Thr Ala Met Tyr Tyr Cys Ala
                85                  90                  95

Lys Gly Ala Gly Pro Thr Trp Trp Tyr Ala Leu Asp Ala Trp Gly Gln
            100                 105                 110

Gly Thr Leu Val Thr Val Ser Ser
        115                 120

<210> SEQ ID NO 8
<211> LENGTH: 111
<212> TYPE: PRT
<213> ORGANISM: Homo sapiens
<220> FEATURE:
<223> OTHER INFORMATION: synthetic

<400> SEQUENCE: 8

Asp Ile Gln Leu Thr Gln Ser Pro Ser Ser Val Ser Val Ser Val Gly
1               5                   10                  15

Glu Arg Val Thr Ile Asp Cys Lys Ser Ser Gln Ser Val Leu Ser Ala
            20                  25                  30

Ser Asn Thr Tyr Leu Asn Trp Tyr Gln Gln Lys Pro Gly Gln Ala Pro
        35                  40                  45

Gln Leu Leu Ile Tyr Tyr Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Val Tyr Tyr Cys Gln Gln Ala Tyr
                85                  90                  95

Arg Ala Pro Val Thr Phe Gly Gln Gly Thr Lys Leu Glu Ile Lys
            100                 105                 110

<210> SEQ ID NO 9
<211> LENGTH: 450
<212> TYPE: PRT
<213> ORGANISM: Homo sapiens
<220> FEATURE:
<223> OTHER INFORMATION: synthetic

<400> SEQUENCE: 9

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Thr Thr His Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Leu Asn Ser Leu Arg Ala Glu Asp Thr Ala Met Tyr Tyr Cys Ala
                85                  90                  95

Lys Gly Ala Gly Pro Thr Trp Trp Tyr Ala Leu Asp Ala Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Pro Val Ala Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp

```
                370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 10
<211> LENGTH: 218
<212> TYPE: PRT
<213> ORGANISM: Homo sapiens
<220> FEATURE:
<223> OTHER INFORMATION: synthetic

<400> SEQUENCE: 10

Asp Ile Gln Leu Thr Gln Ser Pro Ser Ser Val Ser Val Ser Val Gly
1               5                   10                  15

Glu Arg Val Thr Ile Asp Cys Lys Ser Ser Gln Ser Val Leu Ser Ala
                20                  25                  30

Ser Asn Thr Tyr Leu Asn Trp Tyr Gln Gln Lys Pro Gly Gln Ala Pro
            35                  40                  45

Gln Leu Leu Ile Tyr Tyr Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Val Tyr Tyr Cys Gln Gln Ala Tyr
                85                  90                  95

Arg Ala Pro Val Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215
```